US007662549B1

(12) United States Patent
Markl et al.

(10) Patent No.: US 7,662,549 B1
(45) Date of Patent: Feb. 16, 2010

(54) METHYLATION ALTERED DNA SEQUENCES AS MARKERS ASSOCIATED WITH HUMAN CANCER

(75) Inventors: Isabel D. C. Markl, San Francisco, CA (US); Peter A. Jones, La Cañada, CA (US); Yoshitaka Tomigahara, Osaka (JP); Gangning Liang, Rowland Heights, CA (US); Hualin Fu, Los Angeles, CA (US); Jonathan Cheng, Monterey Park, CA (US)

(73) Assignee: The University of Southern California, Los Angeles, CA (US)

( * ) Notice: Subject to any disclaimer, the term of this patent is extended or adjusted under 35 U.S.C. 154(b) by 0 days.

(21) Appl. No.: 09/699,243

(22) Filed: Oct. 27, 2000

(51) Int. Cl.
*C07H 21/04* (2006.01)
*C12Q 1/68* (2006.01)

(52) U.S. Cl. .................... 435/6; 435/91.1; 435/91.2; 536/23.1; 536/24.3

(58) Field of Classification Search .................... 435/6; 536/23.1
See application file for complete search history.

(56) References Cited

U.S. PATENT DOCUMENTS 5,786,146 A 7/1998 Herman et al.

FOREIGN PATENT DOCUMENTS

WO WO 98/56952 12/1998
WO WO 00/26401 5/2000

OTHER PUBLICATIONS

Pao et al. (Human Molecular Genetics, vol. 10, No. 9, pp. 903-910).*
Cameron et al. (Blood, vol. 94, No. 7, pp. 2445-2451, Oct. 1999).*
Database EMBL Online! Aug. 2, 2000 Young, JP et al., *Homo sapiens hyperplastic polyposis proteins (HPP1) gene, 5' UTR and partial cds.* XP002366588 retrieved from EBI Database accession No. AF264150.1.
Young et al., HPP1: A transmembrane protein-encoding gene commonly methylated in colorectal polyps and cancers, Proc. Natl. Acad. Sci., 98:265-270, 2001.
Liang et al., The gene for a novel transmembrane protein containing epidermal growth factor and follistatin domains is frequently hypermethylated in human tumor cells, Cancer Res. 60:4907-4912, 2000.
Szyf, M., The DNA methylation machinery as a therapeutic target, Current Drug Targets, Jul. 2000, pp. 101-118.
Toyota et al., Identification of differentially methylated sequences in colorectal cancer by methylated CpG island amplification, Cancer Res. 59:2307-2312, 1999.
Gonzalgo and Jones, Rapid quantification of methylation differences at specific sites using methylation-sensitive single nucleotide primer extension (Ms-SNuPE), Nucl. Acids Res., 25:2529-2531, 1997.
Antequera et al., "High Levels of De Novo Methylation and Altered Chromatin Structure at CpG Islands in Cell Lines," Cell, Aug. 10, 1990, pp. 503-514, vol. 62, No. 3.
Antequera et al., "Number of CpG islands and genes in human and mouse," The Proceedings of the National Academy of Sciences, Dec. 1993, pp. 11995-11999, vol. 90.
Bird, "CpG-rich islands and the function of DNA methylation," Nature, May 15, 1986, pp. 209-213, vol. 321, No. 6067.
Bird, "The Essentials of DNA Methylation," Cell, Jul. 10, 1992, pp. 5-8, vol. 70, No. 1.
Cedar, "DNA Methylation and Gene Activity," Cell, Apr. 8, 1988, pp. 3-4, vol. 53, No. 1.
Counts et al., "Hypomethylation of DNA: An Epigenetic Mechanism Involved in Tumor Promotion," Molecular Carcinogenesis, Dec. 1994, pp. 185-188, vol. 11, No. 4.
Cross et al., "CpG islands and genes," Current Opinion in Genetics and Development, Jun. 1995, pp. 309-314, vol. 5, No. 3.
Delgado et al., "Initiation of DNA replication at CpG islands in mammalian chromosomes," The EMBO Journal, 1998, pp. 2426-2435, vol. 17, No. 8.
Eads et al., "CpG Island Hypermethylation in Human Colorectal Tumors Is Not Associated with DNA Methyltransferase Overexpression," Cancer Research, May 15, 1999, pp. 2302-2306, vol. 59.
Frommer et al, "A genomic sequencing protocol that yields a positive display of 5-methylcytosine residues in individual DNA strands," The Proceedings of the National Academy of Sciences, Mar. 1992, pp. 1827-1831, vol. 89.
Gardiner-Garden et al., "CpG Islands in Vertebrate Genomes," The Journal of Molecular Biology, 1987, pp. 261-282, vol. 196.
Gonzalez-Zulueta et al., "Methylation of the 5' CpG Island of the p16/CDKN2 Tumor Suppressor Gene in Normal and Transformed Human Tissues Correlates with Gene Silencing," Cancer Research, Oct. 15, 1995, pp. 4531-4535, vol. 55.
Gonzalgo et al., "Identification and Characterization of Differentially Methylated Regions of Genomic DNA by Methylation-sensitive Arbitrarily Primed PCR," Cancer Research, Feb. 15, 1997, pp. 594-599, vol. 57.
Herman et al., "Methylation-specific PCR: A novel PCR assay for methylation status of CpG islands," The Proceedings of the National Academy of Sciences, Sep. 1996, pp. 9821-9826, vol. 93.
Kawai et al., "Comparison of DNA Methylation Patterns among Mouse Cell Lines by Restriction Landmark Genomic Scanning," Molecular and Cellular Biology, Nov. 1994, pp. 7421-7427, vol. 14, No. 11.
Laird et al., "DNA methylation and cancer," Human Molecular Genetics, 1994, pp. 1487-1495, vol. 3.

(Continued)

*Primary Examiner*—Jeanine A Goldberg
(74) *Attorney, Agent, or Firm*—Barry L. Davison; Davis Wright Tremaine LLP

(57) ABSTRACT

There is disclosed 103 novel methylation-altered DNA sequences ("marker sequences") that have distinct methylation patterns in cancer, compared to normal tissue. In many instances, these marker sequences represent novel sequences not found in the GenBank data base, and none of these marker sequences have previously been characterized with respect to their methylation pattern in human cancers including, but not limited to those of bladder and prostate. These 103 sequences have utility as diagnostic, prognostic and therapeutic markers in the treatment of human cancer, and as reagents in kits for detecting methylated CpG-containing nucleic acids.

9 Claims, No Drawings

OTHER PUBLICATIONS

Larsen et al., "CpG Islands as Gene Markers in the Human Genome," Genomics, Aug. 1992, pp. 1095-1107, vol. 13, No. 4.

Li et al., "Targeted Mutation of the DNA Methyltransferase Gene Results in Embryonic Lethality," Cell, Jun. 12, 1992, pp. 915-926, Voume 69, No. 6.

Sadri et al., "Rapid analysis of DNA methylation using new restriction enzyme sites created by bisulfite modification," Nucleic Acids Research, 1996, pp. 5058-5059, vol. 24, No. 24.

Schorderet et al., "Analysis of CpG suppression in methylated and nonmethylated species," The Proceedings of the National Academy of Sciences, Feb. 1992, pp. 957-961, vol. 89.

Xiong et al., "COBRA: a sensitive and quantitative DNA methylation assay," Nucleic Acids Research, 1997, pp. 2532-2534, vol. 25, No. 12.

* cited by examiner

METHYLATION ALTERED DNA SEQUENCES AS MARKERS ASSOCIATED WITH HUMAN CANCER

STATEMENT REGARDING FEDERALLY-SPONSORED RESEARCH

This invention was made with government support under Contract No. CA083867 awarded by the National Institutes of Health. The Government has certain rights in the invention.

TECHNICAL FIELD OF THE INVENTION

The present invention relates to novel human DNA sequences that exhibit altered methylation patterns (hypermethylation or hypomethylation) in cancer patients. These novel methylation-altered DNA sequences are useful as diagnostic, prognostic and therapeutic markers for human cancer.

BACKGROUND OF THE INVENTION

The identification of early genetic changes in tumorigenesis is a primary focus in molecular cancer research. Characterization of the nature and pattern of cancer-associated genetic alterations will allow for early detection, diagnosis and treatment of cancer. Such genetic alterations in vertebrates fall generally into one of three categories: gain or loss of genetic material; mutation of genetic material; or methylation at cytosine residues in CpG dinucleotides within "CpG islands." Among these, DNA methylation is uniquely reversible, and changes in methylation state are known to affect gene expression (e.g., transcriptional initiation of genes where CpG islands located at or near the promoter region) or genomic stability.

Methylation of CpG dinucleotides within CpG islands. DNA, in higher order eukaryotic organisms, is methylated only at cytosine residues located 5' to guanosine residues in CpG dinucleotides. This covalent modification of the C-5 position of the cytosine base by the enzyme DNA (cytosine-5)-methyltransferase results in the formation of 5-methylcytosine (5-mCyt), and gives this base unique properties (e.g., susceptibility to undergo spontaneous deamination). This enzymatic conversion is the only epigenetic modification of DNA known to exist in vertebrates, and is essential for normal embryonic development (Bird, A. P., *Cell* 70:5-8, 1992; Laird & Jaenisch, *Human Molecular Genetics* 3:1487-1495, 1994; Li et al., *Cell* 69:915-926, 1992).

The presence of 5-mCyt at CpG dinucleotides has resulted in the 5-fold depletion of this sequence in the genome during the course of vertebrate evolution (Schroderet & Gartler, *Proc. Nat. Acad. Sci. USA* 89:957-961, 1992), presumably due to spontaneous deamination of 5-mCyt to Thymidine. Certain areas of the genome, however, do not show such depletion, and are referred to as "CpG islands" (Bird, A. P., *Nature* 321:209-213, 1986; Gardiner-Garden & Frommer, *J. Mol. Biol.* 196:261-282, 1987). These CpG islands comprise only approximately 1% of the vertebrate genome, yet account for about 15% of the total number of genomic CpG dinucleotides (Antequera & Bird, *Proc. Nat. Acad. Sci. USA* 90:11995-11999, 1993). CpG islands contain the expected (i.e., the non-evolutionarily depleted) frequency of CpGs (with an Observed/Expected Ratio[1]>0.6), are GC-rich (with a GC Content[2]>0.5) and are typically between about 0.2 to about 1 kb in length.

[1] Calculated as: [number of CpG sites/(number of C bases×number of G bases)]×band length for each fragment.
[2] Calculated as: (number of C bases+number of G bases)/band length for each fragment.

Methylation within CpG islands affects gene expression. CpG islands are located upstream of many housekeeping and tissue-specific genes, but may also extend into gene coding regions (Cross & Bird, *Current Opinions in Genetics and Development* 5:309-314, 1995; Larsen et al., *Genomics* 13:1095-1107, 1992). The methylation of cytosines within CpG islands in somatic tissues is believed to affect gene expression. Methylation has been inversely correlated with gene activity and may lead to decreased gene expression by a variety of mechanisms including inhibition of transcription initiation (Bird, A. P., *Nature* 321:209-213, 1986; Delgado et al., *EMBO Journal* 17:2426-2435, 1998), disruption of local chromatin structure (Counts & Goodman, *Molecular Carcinogenesis* 11:185-188, 1994; Antequera et al., *Cell* 62:503-514, 1990), and recruitment of proteins that interact specifically with methylated sequences and thereby directly or indirectly prevent transcription factor binding (Bird, A. P., *Cell* 70:5-8, 1992; Counts & Goodman, *Molecular Carcinogenesis* 11:185-188, 1994; Cedar, H., *Cell* 53:3-4, 1988). Many studies have demonstrated the effect of methylation of CpG islands on gene expression (e.g., the CDKN2A/p16 gene; Gonzalez-Zulueta et al., *Cancer Research* 55:4531-4535, 1995), but most CpG islands on autosomal genes remain unmethylated in the germline, and methylation of these islands is usually independent of gene expression. Tissue-specific genes are typically unmethylated in the respective target organs but are methylated in the germline and in non-expressing adult tissues, while CpG islands of constitutively expressed housekeeping genes are normally unmethylated in the germline and in somatic tissues.

Methylation within CpG islands affects the expression of genes involved in cancer. Data from a group of studies show the presence of altered methylation in cancer cells relative to non-cancerous cells. These studies show not only alteration of the overall genomic levels of DNA methylation, but also changes in the distribution of methyl groups. For example, abnormal methylation of CpG islands that are associated with tumor suppressor genes or oncogenes within a cell may cause altered gene expression. Such altered gene expression may provide a population of cells with a selective growth advantage and thereby result in selection of these cells to the detriment of the organism (i.e., cancer).

Insufficient correlative data. Unfortunately, the mere knowledge of the basic existence of altered methylation of CpG dinucleotides within CpG islands of cancer cells relative to normal cells, or of the fact that in particular instances such methylation changes result in altered gene expression (or chromatin structure or stability), is inadequate to allow for effective diagnostic, prognostic and therapeutic application of this knowledge. This is because only a limited number of CpG islands have been characterized, and thus there is insufficient knowledge, as to which particular CpG islands, among many, are actually involved in, or show significant correlation with cancer or the etiology thereof. Moreover, complex methylation patterns, involving a plurality of methylation-altered DNA sequences, including those that may have the sequence composition to qualify as CpG islands, may exist in particular cancers.

Therefore there is a need in the art to identify and characterize specific methylation altered DNA sequences, and to correlate them with cancer to allow for their diagnostic, prognostic and therapeutic application.

SUMMARY OF THE INVENTION

The present invention provides for a diagnostic or prognostic assay for cancer, comprising: obtaining a tissue sample from a test tissue; performing a methylation assay on DNA derived from the tissue sample, wherein the methylation assay determines the methylation state of a CpG dinucleotide within a DNA sequence of the DNA, and wherein the DNA sequence is a sequence selected from the group consisting of sequences of SEQ ID NOS:1-103, sequences having a nucleotide sequence at least 90% identical to sequences of SEQ ID NOS:1-103, CpG island sequences associated with sequences of SEQ ID NOS:1-103, CpG island sequences associated with sequences having a nucleotide sequence at least 90% identical to sequences of SEQ ID NOS:1-103, and combinations thereof, wherein the CpG island sequence associated with the sequence of the particular SEQ ID NO is that contiguous sequence of genomic DNA that encompasses at least one nucleotide of the particular SEQ ID NO sequence, and satisfies the criteria of having both a frequency of CpG dinucleotides corresponding to an Observed/Expected Ratio >0.6, and a GC Content >0.5; and determining a diagnosis or prognosis based, at least in part, upon the methylation state of the CpG dinucleotide within the DNA sequence. Preferably, the DNA sequence is a sequence selected from the group consisting of CpG island sequences associated with sequences of SEQ ID NOS:1-103, CpG island sequences associated with sequences having a nucleotide sequence at least 90% identical to sequences of SEQ ID NOS:1-103, and combinations thereof. Preferably, the DNA sequence is a sequence selected from the group consisting of CpG island sequences associated with sequences of SEQ ID NOS:2, 4, 6, 7, 9-16, 19, 20, 22-33, 35-43, 48, 51-55, 59, 60, 64, 71, 76, 78-81, 84 and 87-90, and combinations thereof. Preferably, the methylation assay procedure is selected from the group consisting of MethyLight, MS-SnuPE (methylation-sensitive single nucleotide primer extension), MSP (methylation-specific PCR), MCA (methylated CpG island amplification), COBRA (combined bisulfite restriction analysis), and combinations thereof. Preferably, the methylation state of the CpG dinucleotide within the DNA sequence is that of hypermethylation, hypomethylation or normal methylation. Preferably, the cancer is selected from the group consisting of bladder cancer, prostate cancer, colon cancer, lung cancer, renal cancer, leukemia, breast cancer, uterine cancer, astrocytoma, glioblastoma, and neuroblastoma. Preferably, the cancer is bladder cancer, or prostate cancer.

The present invention further provides a kit useful for the detection of a methylated CpG-containing nucleic acid comprising a carrier means containing one or more containers comprising: a container containing a probe or primer which hybridizes to any region of a sequence selected from the group consisting of SEQ ID NOS:1-103, and sequences having a nucleotide sequence at least 90% identical to sequences of SEQ ID NOS:1-103; and additional standard methylation assay reagents required to affect detection of methylated CpG-containing nucleic acid based on the probe or primer. Preferably, the additional standard methylation assay reagents are standard reagents for performing a methylation assay from the group consisting of MethyLight, MS-SNuPE, MSP, MCA, COBRA, and combinations thereof. Preferably, the probe or primer comprises at least about 12 to 15 nucleotides of a sequence selected from the group consisting of SEQ ID NOS:1-103, and sequences having a nucleotide sequence at least 90% identical to sequences of SEQ ID NOS:1-103.

The present invention further provides an isolated nucleic acid molecule comprising a methylated or unmethylated polynucleotide sequence selected from the group consisting of SEQ ID NO:1, SEQ ID NO:5, SEQ ID NO:6, SEQ ID NO:10, SEQ ID NO:12, SEQ ID NO:13, SEQ ID NO:18, SEQ ID NO:24, SEQ ID NO:25, SEQ ID NO:32, SEQ ID NO:34, SEQ ID NO:37, SEQ ID NO:38, SEQ ID NO:42, SEQ ID NO:44, SEQ ID NO:51, SEQ ID NO:52, SEQ ID NO:62, SEQ ID NO:64, SEQ ID NO:65, SEQ ID NO:68, SEQ ID NO:69, SEQ ID NO:70, SEQ ID NO:71, SEQ ID NO:74, SEQ ID NO:76, SEQ ID NO:82, SEQ ID NO:83, SEQ ID NO:84, SEQ ID NO:86, SEQ ID NO:90, SEQ ID NO:92, SEQ ID NO:97, and SEQ ID NO:100. Preferably the nucleic acid is methylated. Preferably, the nucleic acid is unmethylated.

DETAILED DESCRIPTION OF THE INVENTION

Definitions

"GC Content" refers, within a particular DNA sequence, to the [(number of C bases+number of G bases)/band length for each fragment].

"Observed/Expected Ratio" ("O/E Ratio") refers to the frequency of CpG dinucleotides within a particular DNA sequence, and corresponds to the [number of CpG sites/(number of C bases×number of G bases)]×band length for each fragment.

"CpG Island" refers to a contiguous region of genomic DNA that satisfies the criteria of (1) having a frequency of CpG dinucleotides corresponding to an "Observed/Expected Ratio">0.6), and (2) having a "GC Content" >0.5. CpG islands are typically, but not always, between about 0.2 to about 1 kb in length. A CpG island sequence associated with a particular SEQ ID NO sequence of the present invention is that contiguous sequence of genomic DNA that encompasses at least one nucleotide of the particular SEQ ID NO sequence, and satisfies the criteria of having both a frequency of CpG dinucleotides corresponding to an Observed/Expected Ratio >0.6), and a GC Content >0.5.

"Methylation state" refers to the presence or absence of 5-methylcytosine ("5-mCyt") at one or a plurality of CpG dinucleotides within a DNA sequence.

"Hypermethylation" refers to the methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

"Hypomethylation" refers to the methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

"Methylation assay" refers to any assay for determining the methylation state of a CpG dinucleotide within a sequence of DNA.

"MS.AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al., *Cancer Research* 57:594-599, 1997.

"MethyLight" refers to the art-recognized fluorescence-based real-time PCR technique described by Eads et al., *Cancer Res.* 59:2302-2306, 1999.

"Ms-SNuPE" (Methylation-sensitive Single Nucleotide Primer Extension) refers to the art-recognized assay described by Gonzalgo & Jones, *Nucleic Acids Res.* 25:2529-2531, 1997.

"MSP" (Methylation-specific PCR) refers to the art-recognized methylation assay described by Herman et al. *Proc. Natl. Acad. Sci. USA* 93:9821-9826, 1996, and by U.S. Pat. No. 5,786,146.

"COBRA" (Combined Bisulfite Restriction Analysis) refers to the art-recognized methylation assay described by Xiong & Laird, *Nucleic Acids Res*. 25:2532-2534, 1997.

"MCA" (Methylated CpG Island Amplification) refers to the methylation assay described by Toyota et al., *Cancer Res.* 59:2307-12, 1999, and in WO 00/26401A1.

Overview

The present invention provides for 103 DNA sequences (i.e., "marker sequences") having distinct methylation patterns in cancer, as compared to normal tissue. These methylation-altered DNA sequence embodiments correspond to 103 DNA fragments isolated from bladder and prostate cancer patients, and in many instances, represent novel sequences not found in the GenBank database. None of the instant sequence embodiments have previously been characterized with respect to their methylation pattern in human cancers including, but not limited to, those of the bladder and prostate. The significance of such methylation patterns lies in the value of altered fragments as potential prognostic, diagnostic and therapeutic markers in the treatment of human cancers.

Identification of Methylation-Altered Marker Sequences in Genomic DNA

The MS.AP-PCR technique was used to scan the genomes of bladder or prostate cancer patients for DNA methylation changes relative to normal individuals, because the pattern is known to be highly conserved. A total of 103 DNA sequence embodiments (methylation-altered DNA sequences; "marker sequences") were isolated and characterized as having distinct methylation patterns in cancer, as compared to normal tissue.

Methods for the Identification of Marker Sequences in Genomic DNA. There are a variety of art-recognized genome scanning methods that have been used to identify altered methylation sites in cancer cells. For example, one method involves restriction landmark genomic scanning (Kawai et al., *Mol. Cell. Biol.* 14:7421-7427, 1994), another involves MCA (methylated CpG island amplification; Toyota et al., *Cancer Res.* 59:2307-12, 1999), and yet another involves MS.AP-PCR (Methylation-Sensitive Arbitrarily-Primed Polymerase Chain Reaction; Gonzalgo et al., *Cancer Res.* 57:594-599, 1997), which allows for a global scan of the genome using CG-rich primers to focus on the regions most likely to contain CpG dinucleotides. The MS.AP-PCR technique used in the present invention is a rapid and efficient method to screen ("scan") for altered methylation patterns in genomic DNA and to isolate specific sequences associated with these changes.

Briefly, genomic DNA from the tissue of bladder or prostate cancer patients was prepared using standard, art-recognized methods. Restriction enzymes (e.g., HpaII) with different sensitivities to cytosine methylation in their recognition sites were used to digest these genomic DNAs prior to arbitrarily primed PCR amplification with GC-rich primers. Fragments that showed differential methylation (e.g., hypermethylation or hypomethylation, based on the methylation sensitivity of the restriction enzyme, or upon DNA sequence analysis or Ms-SNuPE analysis; Gonzalgo & Jones, *Nucleic Acids Res* 25:2529-2531, 1997) were cloned and sequenced after resolving the PCR products on high-resolution polyacrylamide gels. The cloned fragments were used as probes for Southern blot analysis to confirm differential methylation of these regions in the tissue. Methods for DNA cloning, sequencing, PCR, high-resolution polyacrylamide gel resolution and Southern blot analysis are well known by those of ordinary skill in the relevant art.

Results. A total of 500 DNA fragments that underwent either hypermethylation (an increase in the level of methylation relative to normal) or hypomethylation (a decrease in the level of methylation relative to normal) were isolated from the scanned patients genomic DNA. A total of 178 of these fragments were sequenced, of which 103 were novel in that they corresponded to DNA loci whose methylation pattern had not previously been characterized. The corresponding sequences are disclosed as [SEQ ID NOS:1-103], wherein for certain sequences, the letter "n" refers to an undetermined nucleotide base.

Novel marker sequences identified by MS.AP-PCR. Table I shows an overall summary of methylation patterns and sequence data corresponding to the 103 DNA fragments identified by MS.AP-PCR. A total of 103 fragments were sequenced following identification as becoming either hypermethylated (gain of methylation; noted as having a hypermethylation pattern) or hypomethylated (loss of methylation; noted as having a hypomethylation pattern) relative to normal tissue. For the fragments of each category, the "Average GC Content" is shown, calculated as (number of C bases+number of G bases)/band length for each fragment, as well as the average Observed/Expected Ratio ("O/E Ratio"), calculated as [number of CpG sites/(number of C bases×number of G bases)]×band length for each fragment. Additionally, the percent of fragments that qualify as CpG islands is listed, and corresponds to the percentage of all fragments within each category that have sequence compositions that satisfy the criteria of having a "GC Content">0.5 and an "O/E Ratio"> 0.6.

Thus, of these 103 fragments identified by MS.AP-PCR, 60 showed hypermethylation (Table I, upper row; Table II, [SEQ ID NOS:1-60]) while 43 showed hypomethylation (Table I, lower row; Table II, [SEQ ID NOS:61-103]). Moreover, 55 (43 hypermethylated, and 12 hypomethylated) of the 103 fragments correspond to CpG islands (i.e., fulfill the criteria of a GC content >0.5 and an Observed/Expected Ratio >0.6), whereas the other 48 (17 hypermethylated and 31 hypomethylated) fragments do not meet the criteria for CpG islands (see Table II).

TABLE I

Summary of 103 DNA Fragments Identified by MS.AP-PCR

| DNA Fragment Type | Methylation Pattern (relative to normal) | Number of Fragments (103 total) | Average GC Content | Average O/E Ratio | Percent that correspond to CpG Islands |
| --- | --- | --- | --- | --- | --- |
| Hypermethylated Fragments | Hypermethylation | 60 | 0.54 | 0.72 | 72% |

TABLE I-continued

Summary of 103 DNA Fragments Identified by MS.AP-PCR

| DNA Fragment Type | Methylation Pattern (relative to normal) | Number of Fragments (103 total) | Average GC Content | Average O/E Ratio | Percent that correspond to CpG Islands |
|---|---|---|---|---|---|
| Hypomethylated Fragments | Hypo-methylation | 43 | 0.52 | 0.48 | 28% |

Table II shows a summary of methylation pattern and sequence data for each individual sequence embodiment ([SEQ ID NOS:1-103]), corresponding to the 103 DNA fragments identified by MS.AP-PCR. Data for the 103 fragments was divided into either hypermethylated ([SEQ ID NOS:1-60]) or hypomethylated ([SEQ ID NOS:61-103]) categories. Table II also lists, for each sequence embodiment, the corresponding "Fragment Name," fragment "Size" (in base pairs; "bp"), "GC Content," Observed/Expected Ratio ("O/E Ratio"), "Description" (i.e., as a CpG island if criteria are met), "Inventor Initials" (IDCM=Isabel D. C. Markl, J C=Jonathan Cheng, G L=Gangning Liang, H F=Hualin Fu, Y T=Yoshitaka Tomigahara), "Cancer Source," and "Chromosome Match" to the GenBank database. A dash ("-") indicates that no GenBank chromosome match existed, or that only a low-scoring partial match was found. Averages of the "GC Content" and "O/E Ratio," along with the percent of fragments that are CpG islands, are listed after the last member of both the hypermethylated and hypomethylated categories.

Therefore, the present invention provides for 103 DNA fragments and corresponding marker sequence embodiments (i.e., methylation-altered DNA sequences) that are useful in cancer prognostic, diagnostic and therapeutic applications.

Additionally, at least 55 of these 103 sequences correspond to CpG islands (based on GC Content and O/E ration); namely [SEQ ID NOS:2, 4, 6, 7, 9-16, 19, 20, 22-33, 35-43, 48, 51-55, 59, 60, 64, 71, 76, 78-81, 84 and 87-90]. Thus, based on the fact that the methylation state of a portion of a given CpG island is generally representative of the island as a whole, the present invention further encompassed the novel use of the 55 CpG islands associated with [SEQ ID NOS:2, 4, 6, 7, 9-16, 19, 20, 22-33, 35-43, 48, 51-55, 59, 60, 64, 71, 76, 78-81, 84 and 87-90] in cancer prognostic, diagnostic and therapeutic applications, where a CpG island sequence associated with the sequence of a particular SEQ ID NO is that contiguous sequence of genomic DNA that encompasses at least one nucleotide of the particular SEQ ID NO sequence, and satisfies the criteria of having both a frequency of CpG dinucleotides corresponding to an Observed/Expected Ratio >0.6, and a GC Content >0.5.

TABLE II

Summary of MS.AP-PCR Fragments Sequenced

| Methylation Pattern | Fragment Name | Size (bp) | GC Content | O/E Ratio | Description | Inventor Initials | Cancer Source | Chromosome Matches | [SEQ ID NO] |
|---|---|---|---|---|---|---|---|---|---|
| Hyper-methylation category | 11-1A | 510 | 0.44 | 0.74 | | IDCM | Bladder | — | 1 |
| | 14-3B | 313 | 0.58 | 0.74 | CpG Island | IDCM | Bladder | 2 | 2 |
| | 18-2B | 165 | 0.57 | 0.45 | | IDCM | Bladder | 7 | 3 |
| | 24-1B | 601 | 0.51 | 0.72 | CpG Island | IDCM | Bladder | Xp11 | 4 |
| | 26-1B | 801 | 0.48 | 0.56 | | IDCM | Bladder | — | 5 |
| | 26-2C | 204 | 0.50 | 0.63 | CpG Island | IDCM | Bladder | — | 6 |
| | 30-3D | 205 | 0.55 | 1.25 | CpG Island | IDCM | Bladder | 14 | 7 |
| | 32-3E | 597 | 0.57 | 0.10 | | IDCM | Bladder | 20q12-13.1 | 8 |
| | 34-2B | 500 | 0.62 | 0.66 | CpG Island | IDCM | Bladder | 20 | 9 |
| | 34-4B | 343 | 0.70 | 0.81 | CpG Island | IDCM | Bladder | — | 10 |
| | 34-5D | 291 | 0.62 | 0.96 | CpG Island | IDCM | Bladder | 9 | 11 |
| | 34-6A | 266 | 0.64 | 0.93 | CpG Island | IDCM | Bladder | — | 12 |
| | 35-1C | 553 | 0.64 | 0.63 | CpG Island | IDCM | Bladder | — | 13 |
| | 36-2D | 156 | 0.60 | 0.58 | CpG Island | IDCM | Bladder | 10 | 14 |
| | 38-1A | 300 | 0.70 | 0.80 | CpG Island | IDCM | Bladder | 10 | 15 |
| | 38-2B | 196 | 0.56 | 0.89 | CpG Island | IDCM | Bladder | 15 | 16 |
| | 7-8E | 299 | 0.59 | 0.39 | | IDCM | Bladder | 17q21-22 | 17 |
| | 83-4B | 363 | 0.54 | 0.49 | | IDCM | Bladder | — | 18 |
| | 84-1D | 322 | 0.55 | 0.90 | CpG Island | IDCM | Bladder | 7 | 19 |
| | 101-3E | 255 | 0.57 | 0.83 | CpG Island | IDCM | Bladder | 17 | 20 |
| | M1-5A | 406 | 0.45 | 0.96 | | IDCM | Bladder | 1 | 21 |
| | U2-8E | 210 | 0.56 | 0.61 | CpG Island | IDCM | Bladder | 2 | 22 |
| | U12-1A | 310 | 0.56 | 0.81 | CpG Island | IDCM | Bladder | 2 | 23 |
| | U7-4A | 305 | 0.59 | 0.80 | CpG Island | IDCM | Bladder | — | 24 |
| | NU9-5A | 379 | 0.67 | 0.83 | CpG Island | JC | Bladder | — | 25 |
| | 3-17-8-B | 625 | 0.48 | 0.72 | CpG Island | GL | Bladder | 18 | 26 |
| | 4-10-4-A | 499 | 0.55 | 0.30 | CpG Island | GL | Bladder | 7 | 27 |
| | 1-1-1-A | 561 | 0.58 | 0.98 | CpG Island | GL | Bladder | 20 | 28 |
| | 3-17-8-A | 717 | 0.50 | 0.68 | CpG Island | GL | Bladder | 17 | 29 |
| | G145-H | 280 | 0.50 | 1.10 | CpG Island | GL | Bladder | 11 | 30 |
| | 1-1-1-D | 270 | 0.50 | 0.60 | CpG Island | GL | Bladder | 2 | 31 |
| | 1-1-1-C | 347 | 0.65 | 1.25 | CpG Island | GL | Bladder | — | 32 |

TABLE II-continued

Summary of MS.AP-PCR Fragments Sequenced

| Methylation Pattern | Fragment Name | Size (bp) | GC Content | O/E Ratio | Description | Inventor Initials | Cancer Source | Chromosome Matches | [SEQ ID NO] |
|---|---|---|---|---|---|---|---|---|---|
| | G178-A | 342 | 0.55 | 0.85 | CpG Island | GL | Bladder | 2 | 33 |
| | 34-A | 370 | 0.62 | 0.44 | | HF | Prostate | — | 34 |
| | 34-D | 213 | 0.53 | 0.74 | CpG Island | HF | Prostate | 2 | 35 |
| | 35-D | 173 | 0.56 | 0.66 | CpG Island | HF | Prostate | 3 | 36 |
| | 36-A | 369 | 0.67 | 0.70 | CpG Island | HF | Prostate | — | 37 |
| | 40-A | 123 | 0.60 | 1.16 | CpG Island | HF | Prostate | — | 38 |
| | 91-1 | 450 | 0.64 | 0.86 | CpG Island | YT | Bladder | 5 or 16q24.3 | 39 |
| | 93-2 | 593 | 0.51 | 0.68 | CpG Island | YT | Bladder | Xp11 | 40 |
| | 93-3 | 457 | 0.52 | 0.94 | CpG Island | YT | Bladder | Xp22.1-22.3 | 41 |
| | 94-8 | 211 | 0.66 | 0.96 | CpG Island | YT | Bladder | — | 42 |
| | 95-5 | 141 | 0.63 | 0.79 | CpG Island | YT | Bladder | 14 | 43 |
| | 97-5 | 559 | 0.56 | 0.40 | | YT | Bladder | — | 44 |
| | 98-1 | 433 | 0.46 | 0.96 | | YT | Bladder | 1 | 45 |
| | 100-1 | 487 | 0.59 | 0.58 | | YT | Bladder | 14 | 46 |
| | 100-2 | 403 | 0.60 | 0.47 | | YT | Bladder | 3 | 47 |
| | 100-6 | 155 | 0.57 | 0.99 | CpG Island | YT | Bladder | 20 | 48 |
| | 4-2 | 256 | 0.57 | 0.40 | | YT | Bladder | 7 | 49 |
| | 5-8 | 224 | 0.47 | 0.96 | | YT | Bladder | 5 | 50 |
| | 6-4 | 313 | 0.70 | 0.82 | CpG Island | YT | Bladder | — | 51 |
| | 7-6 | 385 | 0.70 | 0.88 | CpG Island | YT | Bladder | — | 52 |
| | 13-3 | 307 | 0.59 | 0.89 | CpG Island | YT | Bladder | 10 | 53 |
| | 15-2 | 182 | 0.62 | 0.92 | CpG Island | YT | Bladder | 13 | 54 |
| | 23-2 | 523 | 0.54 | 0.87 | CpG Island | YT | Bladder | Xp22.1-22.3 | 55 |
| | 39-2 | 795 | 0.46 | 0.64 | | YT | Bladder | 13 | 56 |
| | 40-2 | 438 | 0.62 | 0.51 | | YT | Bladder | 10 | 57 |
| | 41-3 | 611 | 0.47 | 0.70 | | YT | Bladder | 18 | 58 |
| | 105-4 | 291 | 0.58 | 0.71 | CpG Island | YT | Bladder | 5 | 59 |
| | 107-8 | 226 | 0.53 | 0.96 | CpG Island | YT | Bladder | 11 | 60 |
| AVERAGE | | | 0.54 | 0.72 | 72% islands | | | | |
| Hypo-methylation category | 14-2B | 580 | 0.55 | 0.51 | | IDCM | Bladder | 2 | 61 |
| | 16-1B | 633 | 0.56 | 0.39 | | IDCM | Bladder | — | 62 |
| | 18-1B | 703 | 0.45 | 0.35 | | IDCM | Bladder | 17 | 63 |
| | 19-1B | 420 | 0.66 | 0.87 | CpG Island | IDCM | Bladder | — | 64 |
| | 20-1B | 496 | 0.61 | 0.59 | | IDCM | Bladder | — | 65 |
| | 21-2C | 637 | 0.60 | 0.33 | | IDCM | Bladder | 9q34 | 66 |
| | 29-1A | 595 | 0.55 | 0.27 | | IDCM | Bladder | Xp11.23 | 67 |
| | 29-2B | 580 | 0.47 | 0.77 | | IDCM | Bladder | — | 68 |
| | 32-1A | 589 | 0.59 | 0.48 | | IDCM | Bladder | — | 69 |
| | 34-1B | 450 | 0.42 | 0.46 | | IDCM | Bladder | — | 70 |
| | 34-3B | 432 | 0.70 | 0.61 | CpG Island | IDCM | Bladder | — | 71 |
| | 32-2B | 748 | 0.47 | 0.24 | | IDCM | Bladder | 2 | 72 |
| | 32-4B | 599 | 0.57 | 0.15 | | IDCM | Bladder | 20q12-13.1 | 73 |
| | 32-5B | 614 | 0.58 | 0.20 | | IDCM | Bladder | — | 74 |
| | 33-1A | 552 | 0.54 | 0.32 | | IDCM | Bladder | 10 | 75 |
| | 5-1E | 501 | 0.61 | 1.04 | CpG Island | IDCM | Bladder | — | 76 |
| | 6-1A | 826 | 0.55 | 0.36 | | IDCM | Bladder | 22q13.32-13.33 | 77 |
| | 7-5D | 433 | 0.59 | 0.85 | CpG Island | IDCM | Bladder | 5 | 78 |
| | 8-7C | 424 | 0.58 | 0.83 | CpG Island | IDCM | Bladder | 5 | 79 |
| | 30-6D | 285 | 0.63 | 0.72 | CpG Island | IDCM | Bladder | 1 | 80 |
| | 66-2E | 401 | 0.54 | 0.82 | CpG Island | IDCM | Bladder | 16 | 81 |
| | 78-1C | 268 | 0.54 | 0.41 | | IDCM | Bladder | — | 82 |
| | 97-2E | 989 | 0.53 | 0.16 | | IDCM | Bladder | — | 83 |
| | M1-8C | 250 | 0.64 | 0.99 | CpG Island | IDCM | Bladder | — | 84 |
| | M2-5A | 402 | 0.50 | 0.45 | | IDCM | Bladder | 5 | 85 |
| | M1-4P | 595 | 0.43 | 0.41 | | IDCM | Bladder | — | 86 |
| | M12-10A | 304 | 0.53 | 0.76 | CpG Island | IDCM | Bladder | 7 | 87 |
| | M12-12C | 296 | 0.51 | 0.64 | CpG Island | IDCM | Bladder | 17 | 88 |
| | M2-8M | 220 | 0.67 | 0.62 | CpG Island | IDCM | Bladder | 6q27 | 89 |
| | NU4-3A | 273 | 0.63 | 1.02 | CpG Island | JC | Bladder | — | 90 |
| | NU5-2A | 361 | 0.44 | 0.73 | | JC | Bladder | 6q14.3-15 | 91 |
| | 88-5 | 462 | 0.62 | 0.39 | | YT | Bladder | — | 92 |
| | 90-1 | 591 | 0.66 | 0.45 | | YT | Bladder | 19 | 93 |
| | 91-3 | 279 | 0.58 | 0.45 | | YT | Bladder | 5 or 16q24.3 | 94 |
| | 91-4 | 351 | 0.55 | 0.30 | | YT | Bladder | 18q23 | 95 |
| | 91-7 | 171 | 0.61 | 0.59 | | YT | Bladder | 11 | 96 |
| | 89-3 | 743 | 0.55 | 0.43 | | YT | Bladder | — | 97 |
| | 94-2 | 589 | 0.53 | 0.41 | | YT | Bladder | 22q13.31-13.32 | 98 |
| | 94-3 | 538 | 0.53 | 0.49 | | YT | Bladder | 5 or 18 | 99 |
| | 94-4 | 486 | 0.61 | 0.57 | | YT | Bladder | — | 100 |
| | 94-5 | 450 | 0.60 | 0.45 | | YT | Bladder | 1p36.2-36.3 | 101 |
| | 94-6 | 292 | 0.58 | 0.32 | | YT | Bladder | 8 or 9 | 102 |
| | 96-4 | 395 | 0.63 | 0.54 | | YT | Bladder | 9 | 103 |
| AVERAGE | | | 0.52 | 0.48 | 28% islands | | | | |

Diagnostic and Prognostic Assays for Cancer. The present invention provides for diagnostic and prognostic cancer assays based on determination of the methylation state of one or more of the disclosed 103 methylation-altered DNA sequence embodiments. Typically, such assays involve obtaining a tissue sample from a test tissue, performing a methylation assay on DNA derived from the tissue sample, and making a diagnosis or prognosis based thereon.

The methylation assay is used to determine the methylation state of one or a plurality of CpG dinucleotide within a DNA sequence of the DNA sample. According to the present invention, possible methylation states include hypermethylation and hypomethylation, relative to a normal state (i.e., non-cancerous control state). Hypermethylation and hypomethylation refer to the methylation states corresponding to an increased or decreased, respectively, presence 5-methylcytosine ("5-mCyt") at one or a plurality of CpG dinucleotides within a DNA sequence of the test sample, relative to the amount of 5-mCyt found at corresponding CpG dinucleotides within a normal control DNA sample.

A diagnosis or prognosis is based, at least in part, upon the determined methylation state of the sample DNA sequence compared to control data obtained from normal, non-cancerous tissue.

Methylation Assay Procedures. Various methylation assay procedures are known in the art, and can be used in conjunction with the present invention. These assays allow for determination of the methylation state of one or a plurality of CpG dinucleotides (e.g., CpG islands) within a DNA sequence. Such assays involve, among other techniques, DNA sequencing of bisulfite-treated DNA, PCR (for sequence-specific amplification), Southern blot analysis, use of methylation-sensitive restriction enzymes, etc.

For example, genomic sequencing has been simplified for analysis of DNA methylation patterns and 5-methylcytosine distribution by using bisulfite treatment (Frommer et al., *Proc. Natl. Acad. Sci. USA* 89:1827-1831, 1992). Additionally, restriction enzyme digestion of PCR products amplified from bisulfite-converted DNA is used, e.g., the method described by Sadri & Hornsby (*Nucl. Acids Res.* 24:5058-5059, 1996), or COBRA (Combined Bisulfite Restriction Analysis) (Xiong & Laird, *Nucleic Acids Res.* 25:2532-2534, 1997).

COBRA. COBRA analysis is a quantitative methylation assay useful for determining DNA methylation levels at specific gene loci in small amounts of genomic DNA (Xiong & Laird, *Nucleic Acids Res.* 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (*Proc. Natl. Acad. Sci. USA* 89:1827-1831, 1992). PCR amplification of the bisulfite converted DNA is then performed using primers specific for the interested CpG islands, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfonation buffer; DNA recovery regents or kit (e.g., precipitation, ultra-filtration, affinity column); desulfonation buffer; and DNA recovery components.

Preferably, assays such as "MethyLight" (a fluorescence-based real-time PCR technique) (Eads et al., *Cancer Res.* 59:2302-2306, 1999), Ms-SNuPE (Methylation-sensitive Single Nucleotide Primer Extension) reactions (Gonzalgo & Jones, *Nucleic Acids Res.* 25:2529-2531, 1997), methylation-specific PCR ("MSP"; Herman et al., *Proc. Natl. Acad. Sci. USA* 93:9821-9826, 1996; U.S. Pat. No. 5,786,146), and methylated CpG island amplification ("MCA"; Toyota et al., *Cancer Res.* 59:2307-12, 1999) are used alone or in combination with other of these methods.

MethyLight. The MethyLight assay is a high-throughput quantitative methylation assay that utilizes fluorescence-based real-time PCR (TaqMan®) technology that requires no further manipulations after the PCR step (Eads et al., *Cancer Res.* 59:2302-2306, 1999). Briefly, the MethyLight process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the fluorescence detection process, or both.

The MethyLight may assay be used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites.

The MethyLight process can by used with a "TaqMan®" probe in the amplification process. For example, double-stranded genomic DNA is treated with sodium bisulfite and subjected to one of two sets of PCR reactions using TaqMan® probes; e.g., with either biased primers and TaqMan® probe, or unbiased primers and TaqMan® probe. The TaqMan® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical Methy Light-based kit) for MethyLight analysis may include, but are not limited to: PCR primers for specific gene (or methylation-altered DNA sequence or CpG island); TaqMan® probes; optimized PCR buffers and deoxynucleotides; and Taq polymerase.

Ms-SNuPE. The Ms-SNuPE technique is a quantitative method for assessing methylation differences at specific CpG sites based on bisulfite treatment of DNA, followed by single-nucleotide primer extension (Gonzalgo & Jones, *Nucleic Acids Res.* 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Small amounts of DNA can be analyzed (e.g., microdissected pathology sections), and it avoids utilization of restriction enzymes for determining the methylation status at CpG sites. Typical reagents (e.g., as might be found in a typical Ms-SNuPE-based kit) for Ms-SNuPE analysis may include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

MSP. MSP (methylation-specific PCR) allows for assessing the methylation status of virtually any group of CpG sites within a CpG island, independent of the use of methylation-sensitive restriction enzymes (Herman et al. *Proc. Natl. Acad. Sci. USA* 93:9821-9826, 1996; U.S. Pat. No. 5,786,146). Briefly, DNA is modified by sodium bisulfite converting all unmethylated, but not methylated cytosines to uracil, and subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes.

MCA. The MCA technique is a method that can be used to screen for altered methylation patterns in genomic DNA, and to isolate specific sequences associated with these changes (Toyota et al., *Cancer Res.* 59:2307-12, 1999). Briefly, restriction enzymes with different sensitivities to cytosine methylation in their recognition sites are used to digest genomic DNAs from primary tumors, cell lines, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

Kits for Detection of Methylated CpG-containing Nucleic Acid. The reagents required to perform one or more art-recognized methylation assays (including those identified above) are combined with primers or probes comprising the sequences of SEQ ID NOS:1-103, or portions thereof, to determine the methylation state of CpG-containing nucleic acids. For example, the MethyLight, Ms-SNuPE, MCA, COBRA, and MSP methylation assays could be used alone or in combination, along with primers or probes comprising the sequences of SEQ ID NOS:1-103, or portions thereof, to determine the methylation state of a CpG dinucleotide within a genomic sequence corresponding to SEQ ID NOS:1-103, or to CpG island sequences associated with sequences of SEQ ID NOS:1-103, where the CpG island sequence associated with the sequence of the particular SEQ ID NO is that contiguous sequence of genomic DNA that encompasses at least one nucleotide of the particular SEQ ID NO sequence, and satisfies the criteria of having both a frequency of CpG dinucleotides corresponding to an Observed/Expected Ratio >0.6, and a GC Content >0.5.

We claim:

1. A method for detecting breast cancer, comprising:
   (a) obtaining a tissue sample from a test tissue;
   (b) performing a methylation assay on DNA from the tissue sample, wherein the methylation assay determines a methylation state of a plurality of CpG dinucleotides within SEQ ID NO:36; and
   (c) comparing the CpG dinucleotide methylation state of the plurality of CpG dinucleotides within SEQ ID NO:36 in the test sample to that of a control DNA state, wherein hypermethylation of the test sample is indicative of breast cancer.

2. The diagnostic assay of claim 1 wherein the methylation assay procedure is selected from the group consisting of MethyLight, MS-SNuPE, MSP, MCA, COBRA, and combinations thereof.

3. A kit useful for the detection of a methylated CpG-containing nucleic acid comprising a carrier means containing one or more containers comprising:
   (a) a container containing a probe or primer consisting of at least 12 contiguous nucleotides of a sequence selected from the group consisting of SEQ ID NOS:36 and 37, and the bisulfite-converted sequences thereof; and
   (b) additional standard methylation assay reagents, wherein the kit, based at least in part on the probe or primer, is suitable to determine the methylation status of one or more CpG dinucleotides within the sequence selected from the group consisting of SEQ ID NOS:36 and 37.

4. The kit of claim 3, wherein the additional standard methylation assay reagents are standard reagents for performing a methylation assay from the group consisting of MethyLight, MS-SNuPE, MSP, MCA, COBRA, and combinations thereof.

5. An isolated nucleic acid molecule consisting of a methylated or unmethylated polynucleotide sequence selected from the group consisting of sequences of SEQ ID NO:37 and the bisulfite-converted sequences thereof.

6. The nucleic acid of claim 5, wherein the nucleic acid is methylated.

7. The nucleic acid of claim 5, wherein the nucleic acid is unmethylated.

8. A method for detecting prostate, breast or colon cancer, comprising:
   (a) obtaining a tissue sample from a test tissue;
   (b) performing a methylation assay on DNA from the tissue sample, wherein the methylation assay determines a methylation state of a plurality of CpG dinucleotides within SEQ ID NO:37; and
   (c) comparing the CpG dinucleotide methylation state of the plurality of CpG dinucleotides within SEQ ID NO:37 in the test sample to that of a control DNA state, wherein hypermethylation of the test sample is indicative of prostate, breast or colon cancer.

9. The diagnostic assay of claim 8, wherein the methylation assay procedure is selected from the group consisting of MethyLight, MS-SNuPE, MSP, MCA, COBRA, and combinations thereof.

* * * * *

SEQUENCE LISTING

```
<160> NUMBER OF SEQ ID NOS:   103

<210> SEQ ID NO 1
<211> LENGTH: 510
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 1
ttgcaagccc ccttngctct tcctttgncc tcgcctacat attcagggga tcgcaatctc      60
actcgcgaaa taatttnttt ctgtaagagg aagccgcctt tcccctctcc caccgccaag    120
gtaaaggctg ctaaagtagc tcttcttgga aggaaaaata ttttaaaaag cagctgggtt    180
gctctccaca agaagatggc agttttggga aaacccatta tgtgtccaaa tgccggtttc    240
```

```
cttttcttgt taacgctttt ttagagggca aaaatgacgc tcatgtgaag cccacaggct      300
cgagccaatg tcgctgggct aattatgagt ctgcttatcc cactcccaaa tatccgagac      360
gactcactca naagacattt ttactcttcc aagaattgng aattcagaan cagcttcccc      420
acattctaag agaaaaaaaa acttgtttaa cgggcacgtt tttgattttt ttgccgctgg      480
cgaccttaat taaaagccgg gagctncnna                                      510

<210> SEQ ID NO 2
<211> LENGTH: 313
<212> TYPE: DNA
<213> ORGANISM: Homo sapiens

<400> SEQUENCE: 2
gcactcttaa aacgcctctc tgcagtccca ggtccgcgct ccccaagaac tggccagatc       60
gcgccgggct tggcccctga caactctgcc tcctccacct gttgcgttta ctccgtttag      120
ttggctgtgc agtctctggc cccaggtgtg cttttaaaac tcgaggaacg cgggtgttgg      180
actcattcgc agcctcttgc ctctggttcc cgtgatccca cggtggcgag cttccaggct      240
cagcgaggag atctgggttt gaacattcat ctcccatgtt actcttttct tgctcctcgc      300
gtccccaagc cga                                                        313

<210> SEQ ID NO 3
<211> LENGTH: 165
<212> TYPE: DNA
<213> ORGANISM: Homo sapiens

<400> SEQUENCE: 3
gcttagcaaa tttccctttt ttattgttgg ttttgtctgt tggctcttac cccctttcct       60
tttcctgctt cccctgagtc agcaatgctg agcccagcga agcacagggg gccaaaggga      120
gagacacacg gagcgccccg gggtccccca gcctcggcgg ccaaa                     165

<210> SEQ ID NO 4
<211> LENGTH: 601
<212> TYPE: DNA
<213> ORGANISM: Homo sapiens

<400> SEQUENCE: 4
ggggggagtc gtgcgtgtca gatttaggcc aggaagcgga agtcgccagc agcgagagtt       60
taacctctgt gggcgcagag ggttgcgggg attcagcgcc cggaccgtg gatctgtgca      120 gggagtcata ggtgtgtgtg acatcagtgg tggaacattt tggctcgttt tcacaattca      180
gtcattatcc tttctgcttt cctcctggaa gcattaaggt tgaagttttc ttctaaagat      240
caaagttttg atttgttata ttagttcgga tttgtttgat ttttgtttgt gttcggtttc      300
aagtgctgat ttgtaacttt tctccccccc cacacacacg ccttttgacc cctgaattat      360
ttaaaagtcc attgttggag tggcaaacat cctccgagac tcaaagggca aggccatggg      420
cgctttattc cggctgctgc tccaggaacg tgggaaagca gcggagtttt attctagggg      480
aaggaaacaa aggcggccga gtgccagctg cacgtttggt gggatttggt catcaggggt      540
ggacatgctg cccaatggag ctgtcggcag tttgacccag cttggtccgt cgcgtcccga      600
a                                                                     601

<210> SEQ ID NO 5
<211> LENGTH: 801
<212> TYPE: DNA
<213> ORGANISM: Homo sapiens
```

```
<220> FEATURE:
<221> NAME/KEY: misc_feature
<222> LOCATION: ()..()
<223> OTHER INFORMATION: "n" refers to an undetermined base

<400> SEQUENCE: 5
gagtacgcgg ggcagaacca gcgcaataca gcattctggt aggggaacta attttgacta      60
aaatatttgc caattctaat ccccaattcc tggacctccg ggtagctggc aaggtatttt     120
atgttagatg tgtctggagt aaggtgcacc ggagtatttc gacaagagac tcaattcaat     180
gcgtattaaa acttgattga gagagggaga gagagaggtc attttataaa gaaagacctg     240
tgaacactgt agattggaaa tttatgtttg caaaataaaa ggatgggttt atcaagtgga     300
tgcatttaca aaatgtggca tccaggtttc gtaaaattag ctgaattcta cgggtaagat     360
tatgaatgtg gctcataaat aattaatagg tagtgaaaaa gaatgtattt tgcattaggc     420
agtgcattca atagtatttc ggaaatgagc acttcgattt cctcggnttc catgcgnggc     480
cacctctcca gagcagggca ggcacccagg gnggtgccca cacaaacaag cgcgtgtggg     540
cattttcttg gctcgtgcgc tgaagtgcac gctgggcctt ggtgcccgca ccctcagcct     600
gggagatagg gaggtggtgc tacctgcagg ccgattgtgt ccccgccata ggacactagt     660
gggcggcaaa cctcacaaga ctcttgcagc cagccttcag cagagccagc aaacccagcc     720
gccaccgagg gaggactgct ccatgcagat ggtcaggggc tttcttctga agacgcctcc     780
cccacgatct ctcaagttca c                                               801

<210> SEQ ID NO 6
<211> LENGTH: 204
<212> TYPE: DNA
<213> ORGANISM: Homo sapiens

<400> SEQUENCE: 6
ccggttgctg ctggaggatg ggactacgaa ggatggggac tccgctcggc caccgctcct      60
gaatggcctc taatctcggt gttaaatact ttatgagagt atcaatacca cctaatcctt     120
tgctgagaat tactgctaga aatgtagatt ctgaggttcc gaaagtttgt ttttggttac     180
cccctccagc tcctcccgcg gcaa                                            204

<210> SEQ ID NO 7
<211> LENGTH: 205
<212> TYPE: DNA
<213> ORGANISM: Homo sapiens

<400> SEQUENCE: 7
agacctttat cgggcgtgag tgaaatcggt cgttcgtgtt tttcgtgggt cttccaacca      60
caggccgcct gagatggttc tagtcccttt gagtatacag acccttcctg tgcattgacc     120
gacacagctc ggcccggatc ccgaaatgaa cgtttctacc ttcggaacgc tgcgtctcgg     180
atccttctga acccgcacgt cgcaa                                           205

<210> SEQ ID NO 8
<211> LENGTH: 597
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base
```

-continued

```
<400> SEQUENCE: 8
gaccatgaaa tcgtgtggct ctagcccctt ctgggcctct tgttggtaat gaagccactc    60
taaagcgccc cctgttattc agagggctcc ccagctgcca tgatatgtgt atggggaggg   120
catagcaggt cctttttgccc cggcagccat tcttctgctc acaaggggct ggctctgggg   180
acagggatgt ctttgtcatc agtgaccact aatcccccctc ctcattggcc tccagggctg   240
ctccccttca ctctcttggt tgaagttgta ggggctgagg ttaccctgag aaacacctgt   300
tcttggagcc catagaccca accttggaga tgcaggggga gccactggct gggctctgca   360
ngtggggcca gctgatcccc anctgctggc acctccaggc atccacagag cttggagtcc   420
cagccacatt tcctccttgg ccttagaggg agaggaagtc ctttgattgc ctagtccaag   480 atcccttttat ttcctgccct gggattatgg ggnagcaagc catgcccttc atgggaagct   540
gttctccctt cctcggggtt gggtctggcc tcagctcggg caacagtcat gatgggc     597

<210> SEQ ID NO 9
<211> LENGTH: 500
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 9
gccaaacgcn ataccctctg cggggtgaga atgcgggccc gcccggctcc tcccgtgagg    60
ccagggcctc ctgttctcct agacacccca aggagccaac tcctccgcag aagttccccg   120
cttctgctct tatttccaag cttcgcgctt tctacaaact ccctgttgcc ttgactttga   180
tttccagccg tggtgagggt cagagtgaac cccggcgcgc tccccgacgg catccccgca   240
caccaggata ggagaaattg gagggcctgg ggcctcgggc tccgcagtcg tcggaggaag   300
aacccaccgc ggggtccgca agggaaagtg aagaggcccg ggatttttcc aaagcgctgg   360
ccaggacccc gaaggaaggg gaggagtcac ctgaagccgg ggaaggcccc ttgggtgctc   420
tgccttggat cctatgttc actgactttc gcgacccctg gagggggca aatccgcgct   480 gtttccccca acttggcttc                                              500

<210> SEQ ID NO 10
<211> LENGTH: 343
<212> TYPE: DNA
<213> ORGANISM: Homo sapiens

<400> SEQUENCE: 10
gccaacccac accagtacct gggaccgggg ggagcccggt ccggccgcta aaccgggctg    60
gctggcgcca gggctccggg aggtgcggtc cggcggggaa gccgtgatgg gaagcgactc   120
tgtccaggga gtgtccttca ccaccacact cctcacgtcc aggcagtgat cgacggcctg   180
gcggcaccct cacagcgggc ccatagcacg gggccacaca cgtcccctga gcttagcctg   240
ggcacattcg tctgccgccg agggcttaag ccagtctgca gcccgcgccc cgtcactcgg   300
acgcaagtcc gtcgtccgct ctgccacgcg gccgctaagc cga                    343

<210> SEQ ID NO 11
<211> LENGTH: 291
<212> TYPE: DNA
<213> ORGANISM: Homo sapiens
```

<400> SEQUENCE: 11

```
gtcctacaca ctccgcacac aacgcggccg gtgttaagtc tccaaacgcc ccgagagctc      60
caaggaccgc gcgcgcgaag gcgccgtagc aagtgggcac acaccagaca ccaccccggc     120
gtgttccgcg ggagaagcca gtgcacacat cctcccgcaa ggcggggttg ccagtgcaac     180
acaggaatcc tgcccttttt ctagaaaagc cccctccccc actttccctc caatacactc     240
acctgcgtct caacagtttc cttcttgcgc tacacgcggc cgctaagccg a              291
```

<210> SEQ ID NO 12
<211> LENGTH: 266
<212> TYPE: DNA
<213> ORGANISM: Homo sapiens

<400> SEQUENCE: 12

```
gtccggatca gtttccccgg ccaggtcgct tcccggtctc aaccatttcg cgctctgctc      60
tgtccgctgg tttgtccctg cccggttcct ctccccgggc ctgtcagcct ccgcttctct     120
ggaggttcct gggactcatc tctgatccac cgtcttgcgt tctctgggcg catcgacttc     180
tctccatctt cgggctcact cctgactccc tcgctgccgc ccccgggggt ttccacgcgt     240
gtctctaacc gcggccgcta agccga                                          266
```

<210> SEQ ID NO 13
<211> LENGTH: 553
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 13

```
gatcctggtc catcgaaacc ttgtgtgcat cggttagtgc ttcctgggcg tttgcttcta      60
gccgacgctg acagtggagt gccagaaaga gggagaggac cgtcatggct actctgcccc     120
tggtgtcacc atgcgctctc ccccggcacc ggcgaggcga aacgtttcgc tagtccccgg     180
gaggcccctc ggtcagggca gcagcatccc tgcaccctct ccgcaggtgg tctccccgac     240
gccacaggtg gccagcaggg cgcggtgggg ggcaggagcg cctctcccct gcccaggcct     300
cccgctcctt ctcggagcgc tgtggcgggg tggagagaca gccttctaca gctagtctag     360
ctcggcgcgg ttcccgtctg tggcctccta atcccacagc cacagcgcct tcctctaacc     420
tccctcggtg ggcttaaagc ctcccgttcc ttctgtctca ttccttctgc tcctcccccc     480
cgaaaccccc agatganagc tgggaacctg gcnccantna ctgagcnaac agtgttgacg     540
ggccgnggcc caa                                                        553
```

<210> SEQ ID NO 14
<211> LENGTH: 156
<212> TYPE: DNA
<213> ORGANISM: Homo sapiens

<400> SEQUENCE: 14

```
gcgcacacag tgggtacaag gatgagctcg gtgtaaggaa tggaaagccc ccagtctaaa      60
ccaccgcccc ctagacacgg gtgaaaacct gcctaaaagc taactcaggc agtgactcta     120
tcacccgaag gggccctggg ccgcggccca agccga                               156
```

<210> SEQ ID NO 15
<211> LENGTH: 300
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 15

```
gttcacagcc cataaggtgg gggtggcccg aacctgaaac ggagcctgag ccaggatcct      60
gcaaccaaag tctgaagcgc cccccggtgg gggccgagag cgctgcaggc aggtggnggc     120
gcggggcagg cgggcgggcg aagggagctc cggntacgca ganaacgcgg agcgcccct     180
tcccacctgc gcgagggcat cctgcccggg ggaggaaagg cgggagtccg aggcgggtcg     240
gattcccagc cagctccctc ctcacaggag gcggcccatt atccggcgtc gcaaagccga     300
```

<210> SEQ ID NO 16
<211> LENGTH: 196
<212> TYPE: DNA
<213> ORGANISM: Homo sapiens

<400> SEQUENCE: 16

```
ggcgcccagc aggggagcga gggaggaggg tgcagaaaga ggctccgaaa ttgggggaaa      60
ctgacccgtg cttctctacc ttcggaggtg ggacagttgc acgaagtgct agttagaccg     120
gatcagttgg aactgacgga ggactgcaaa gaagaaacta aaatagacgt cgaaagcctg     180
tcctcggcgt cgcaaa                                                     196
```

<210> SEQ ID NO 17
<211> LENGTH: 299
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 17

```
acaccaggag aggggaagaa nccagcacct accgacaggg gtggagctgg gtcaagaatg      60
gtgtggtccc tgctttgggg gaatgctggg gaggtagaaa gccccttcta acggggcgtc     120
actgcaatta ctgcttcctc tttcccataa aactcccccct agtgtatcag aaccccaag     180
gagtttcagt aagcggttct tctgttgtct ccggctgaga ctccagggga acctcaagct     240
cacatggccc tggccgggcc cctgggcagg agcaggcgag aggtctgcgc ggccgctaa      299
```

<210> SEQ ID NO 18
<211> LENGTH: 363
<212> TYPE: DNA
<213> ORGANISM: Homo sapiens

<400> SEQUENCE: 18

```
gggtatgtgt tacacatccg agataactac acaggcatcg accctgtcca cccggggatg      60
ctagaggggc tgcgctggtt ttactccagg ccatggtgag agccaccgtg aacacagggc     120
tctctcctct gagctgcaga agctctgtgc cctgtcccct gccacaagtc acagactttc     180
ttcatgtgtt ttacctcatg ttaatgaagg agatcttctc caggggcttg atctagtggg     240
aaacagagga gggggggatt ttaaatttca gtccgtccaa ccctgtagat ctgctgtcct     300
```

-continued

```
acagtaacgt aaaggatcac caggtaaaac gctgcttctc ccggacgccg ccccgcaagc    360
cga                                                                  363

<210> SEQ ID NO 19
<211> LENGTH: 322
<212> TYPE: DNA
<213> ORGANISM: Homo sapiens

<400> SEQUENCE: 19
ccggcccgtc cctcttaata tggcctcagt tccgaaaacc acagaataga accgcggtcc     60
tattccatta ttcctagctg aggtatccag gcggctcgga cctgctttga acactctaat   120
tttttcaaag taaacgcttc gggctgcagg acactcagct aagagcatca gggggcgcc    180 aagaggcaag gggcggggat gggtggtggc tcgcctcgtg gcagaccgcc cgcccgctcc   240
caagatccaa ctacgagctt tttaactgca gcaactttaa tatacgctat tggagctgga   300
attaccgcgg ccgctaagcc ga                                            322

<210> SEQ ID NO 20
<211> LENGTH: 255
<212> TYPE: DNA
<213> ORGANISM: Homo sapiens

<400> SEQUENCE: 20
taataagata ccaaatcggg cgagaaacga aaagctcctg gcctccgtat ttggggccag    60
agacaccgca gggagtcagg tccccgccga caaatcggaa gaggcctgcg ggagttagcc   120
agataatgct ctccctgtcc tacccgtccc caccaatttg ccttttacct gccgcagagc   180
ttgcttgaac caaagggggtt tgcggtcttc tcctcctcaa cttgcgatcc ccaggccttc   240
gcgtcccgaa gccga                                                    255

<210> SEQ ID NO 21
<211> LENGTH: 406
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 21
atgtgnnaag gctcgctntc catttctctt ttcctccttc tccctctctc atgtgcggtc     60
tccctcaaca tccaaaccaa ccgagtgcgt ctgaggtgaa atcgtgccag acttagagac   120
ggctgccagg tttctctcaa gtcttggctt aacaaaagaa agcaaattac aaaaatggaa   180
attttcaaac tagcgttcag tggtattcaa atcgacgttt gggtagcgca caggcacaga   240
ccgcattcgt gctattttgt gattaaaatg ataccaaaaa tacctccttg ctttggtttt   300
cgtcttcgaa aacgacttct ttccttcttc taatttcccc cttactttg ggagcggcaa    360 accctgacc actctagaat tgctaacatt tggaccggcg tcgcaa                   406

<210> SEQ ID NO 22
<211> LENGTH: 210
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base
```

```
<400> SEQUENCE: 22
gcacgttcgn gcnncgtgta ccatnagctg ccaactggan gcaccnnggn aagggtgggg     60
gcctcctgga gacttngggg agagggatag ccggntaaag ctcctgtcct ttctataggc    120
ataagcgggt ggtcaccacg gattggggat cccgaatccc tggctccaga tagacttaat    180
gaagaagcac ctggatccgg gccgcgncaa                                     210

<210> SEQ ID NO 23
<211> LENGTH: 310
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 23
tcacgcttnc naaggctctg aatcctgagg gncagatctc caagaaggag ggaggctggt     60
cctagttccc gaggtcctnn actaggtcta gatcactggg taaaagaagg ggagcggcan    120
cacgtatggg gtaggcgctc tcactactca catctcgaga cctttgccgg cgtagggctg    180
tccgggggga acgacccgcc ttttccggta tcggttgtca tggcggcgcc cagcccagcc    240 tggtttttc cggtagccaa ttgaactaac aaccccgttc cctttaggac taatctgtca    300
cgtcggcgca                                                           310

<210> SEQ ID NO 24
<211> LENGTH: 305
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 24
ctctggtctg tgntggatac gcgtgttctt ctgcggagtt aaagggtcgg ggacggggt     60 tctggactta ccanagcaat tccagccggt gggcgtttgg cagtcactta aggaggtagg    120
gaaagcagcg agcttcaccg ggcgggctac gatgagtagc atgacgggca gcagcagcag    180
ccagcaaaag ccctcgcaaa gtgtccagct gctgcactgc cgcggggact cccacagcac    240
catgactagt tcgtgcgact ctgcancanc aaacggcttc cgaggaacac angatcgcgg    300
gggca                                                                305

<210> SEQ ID NO 25
<211> LENGTH: 379
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 25
aaaacncatn tgnagagcnc ntcggcagag ncgcagctgg ctgacccagg agaaggcgcg     60
ctgggtgtgg ctgggacggc caaggccgcg gcttcccgcg tggggatgcg ctntggcgca    120
aagctggtcc cggcggggcc aggcgtttgt gggcgggtga cggggatcta gggcttccgc    180
tcgngattcc tcttggcctg tctttncggg tttggactcg cctgccaggc tgtgtgcagg    240
gttcccgctg cctctggccg gcaggcgtcc gggctgcagg tgggccggca ggcaggtgtt    300
```

```
agcgggaagg gagcacaggt agcgaggtgg gatcggcgac ctggctaggg tgtcggcaga    360
atggaatgcg cggccgcta                                                379

<210> SEQ ID NO 26
<211> LENGTH: 625
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 26
gggacgcnag ccagggantt tgatccgttt tgaatgaaaa gaaagagaan ccaaaccaaa     60
cctntcagtc atccaaaacc ttcaggcttc cagggaggtt ttgctataat tttctctaag    120
catgactgtt tctgggggag gggaaagggg tggttgtatt tactgaaaat tcaaatcgaa    180
ataataaatg gccaaatttg gacacttacg gacccaaaca gttttgctca cgccagagaa    240
accgagagca cagggcttgc gtgaagccta tctcggcaga aggcaacatt ctaataaagc    300
ccgtgggaaa acagattaca ttttcgccat gaataagtca tgcagtgaaa aatattgcct    360
acagcctgtc gacttatatt attatcacgt ttttcaactc ggcgtgagga gggagaggag    420
tgttcatatt tgactaggaa ttgcaggatc gatgcaaact ccaggcagc agccagactg     480 gcatatgtgg ggctctccgg ttactttctc tgtatgtcgc gggtgagagg aacagcgagg    540
acaatttagc gcaaacacac gaagggtcgg atctcaaggg ggcagcgctg ggagaaaggt    600
tagggctgna gagcgnanag ncaaa                                         625

<210> SEQ ID NO 27
<211> LENGTH: 499
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 27
gnctccncgt tccctcggg cggaacggag gcaactttcc ggagtctatt tttgttaaga     60
caatcaactc caataactga gctgaagttt tgtttaaaa agaaaaaaat ctgataagtg    120
atgattttac ctacttgtgg acactagatt tcaattagga aggttttttt aaacggcttt    180
ttgtaacttc gctgcaggaa gcaggtttgt ttcttttttct tttctttta agagaaggtg    240 tatttcactg gtgcaatggc ttggcacctc cggggcctgg gaggacctca gacctccca    300 gccctgggtt tctccgtctt caagaccaac taggaagggt caagcgggga gagggagtgg    360
agggtcaggt gagatctcag agctgccccg gccggccccc gtctctttct acctcctctt    420
ccagagaacc agcggctcac acccttctca acgcaggaca tgctcggcgg ccaaagccga    480
attctgcaga tatccatca                                               499

<210> SEQ ID NO 28
<211> LENGTH: 561
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base
```

<400> SEQUENCE: 28

```
gggcgattgt tattcaaacn ngntanctct ctgcggggnn gagnaatgng ggcctcgcac      60
ggctncatcc ccgtcgagcn cagggcctcc ctgttctnct agacatncca aggagccaac     120
tcctccgcag aagttccccg cttctgctct tatttccaag cttcgcgctt tctacaaact     180
ccctgttgcc ttgactttga tttccagccg tggtgagggt cagagtgaac cccggcgcgc     240
tccccgacgg catccccgca caccaggata ggagaaattg gagggcctgg gcctcggctc     300
ccgcagtcgt cggaggaaga acccaccgcg gggtccccaa gggaaagtga agaggcccgg     360
gattttccca aagcgctgcc aggaccccga aggaagggga ggagtcacct gaagccgggg     420
aagctccttg ggtgctctcc ttggatcctt atgttcactg actttcgcga ngcccctgg      480 aggnggaaaa tccgcgctgt tcccccaac ttaacttcac gcggccgcta agccgaattc      540
tgcngaaatc attacactng c                                              561
```

<210> SEQ ID NO 29
<211> LENGTH: 717
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 29

```
actctccgcg gtntcntggt gcctcacagg aggtggggct ccctccaccc ggtccccagg      60
cctctccctc tgcccgagct tcccggtcct gcctccttcg cctcgcctgc ctgcccgact     120
ctgaaccctg ctcctcttct aactaaaagt cagtgtttta tttcctccgc agtccaatgc     180
ccgcgtttta ccttattcaa taagaagggc ttcatttatg gcaagacagg acagccaggt     240
aataagggcc tctgcacacg cgggcccatt ggaggggcgg aactgcgaag tcttcccgga     300
agagcttcct ggagagaagg ggaacgagcc agcgtttatt gagcatctat tatactaagc     360
atctgcttgg cagttcacga cggtcgcatt ttttcatcct tacagcgatc cctattgtgt     420
cgcttgcttt aaagcctcac agctcacaaa gggctgggat ttattccaga tctctctctc     480
agatgccatc tcacttccag gtgtctctgc tgctttgaac gcgggaaacc cacgcaaagg     540
agtgatttcc aaggccttct gtttggaata tctttaatcc tcccttatt aactggaaaa      600 actcccacgc atccttcagg gctcagctca aatgtccttt atntctgcag ngaaactttc     660
ccaaggaaaa ttagttacac agctaatttt agataaattg agccagttga tagaatt       717
```

<210> SEQ ID NO 30
<211> LENGTH: 280
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 30

```
tgatggatat ctgcagaatt cgggctttgn gacgccgggc acgcagtagg gaaaacagta      60
ttaaaacgcc ctacagaaaa tctcggcgaa gtccccggag aactctggtt tctaagatca     120
gctgggcgca ctttctccgg gacgtccctt cttctcggtc tcagcgcctt cctgccctca     180
gccgcgccng tnttgttttg gtggcaaact gaaataagaa atggaaatat attggccttt     240
gctgctgcca gggatgagag gttgttgacg tcggcgcaaa                          280
```

<210> SEQ ID NO 31
<211> LENGTH: 270
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 31
gnggnngnna nncggcgatg gatntnngna ganttnggtg atggatatct gcagaattcg      60
gcttagcggc cgcgaacaaa gagcgaacca aaggatgctt cgaattttta aaacggaatc     120
tctgcaccca aatgcaggac tggtgactta aggagctgcg aagtctgatt taccgggcct    180
actctcgacc tgcccccccac ccccagctca gggggacctt tttatcntga acgccagagc    240
tacnnaccaa gtcgggtggc cacnnccaaa                                      270

<210> SEQ ID NO 32
<211> LENGTH: 347
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 32
tttggannta nggggcgtg gcgtggatcc agtttccccc ggccaggtcn gcttcccggt      60
ctcaaccatt tcgcgctctg ctctgtccgc tggtttgtcc ctgcccggtt cctctccccg    120
ggcctgtcag cctccgcttc tctggaggtt cctgggactc atctctgatc caccgtcttg    180
cgttctctgg gcgcatcgac ttctctccat cttcgggctc actcctgact ccctcgctgc    240
cgccccgggg gtttccacgc gtgtctctaa ccgcggccgc taagccgaat tctgcagata    300
tccatcacng aantctgcag anatncatcg ncgaannnca ccgcact                  347

<210> SEQ ID NO 33
<211> LENGTH: 342
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 33
gtagggcgcc gccgtgacag attagtccta aagggaacgg ggttgttagt tcaattggct      60
accggaaaaa accaggctgg gctgggcgcc cgccatgaca accgataccg gaaaaggcgg    120
gtcgttcccc ccggacagcc ctacgccggc aaaggtctcg agatgtgagt agtgagagcg    180
cctaccccat acngtcggcc ggctcccctt cttttaccca gtgatctaga cctagtctag    240
gacctcggga actaggacca gcctccctcc ttcttggaga tctgaccctc aggattcann    300
nnctttgctc acgagctcca acccnacnca tccaaannnc aa                       342

<210> SEQ ID NO 34
<211> LENGTH: 370
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

```
<400> SEQUENCE: 34
cattgtttac tttcgtctaa acgcggtgga agcccatgga agaaagcggt tagcagcaag        60
gcagagccct gctccctctg cagccccagc tcccagcgcc ctgggctttc caggcacctg       120
tccgggtagg ggattgaggg ccgtggccag gcccgcactt tcctgctagc cgcagctggc       180
cacatgccca tctgaccctc cgagttctcc tctaaaaatg gggctgacag ccgctacctc       240
acaaagtcca caccgggctc aacccgntgc cttcctcccc aacaggactc tgccaccctc       300
cctcaggatg cctgagggcc ccganctgca cctggccagc cantttgtga atgaggcctg       360 ngggcgntt                                                                370

<210> SEQ ID NO 35
<211> LENGTH: 213
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 35
aaaatacnan taaagcgatg cttcgaattt ttaaaacgga atctctgcac ccaaatgcag        60
gactggtgac ttaaggagct gcgaagtctg atttaccggc ctactctcga cctgcccccc       120 accccccagct caggggacct tttgtctgaa cgccagagct actgaccagg tcgggggcc      180 gcggcccaag ccgaattctg cagatatcca tca                                    213

<210> SEQ ID NO 36
<211> LENGTH: 173
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 36
gacnncgggt ttgtgtgtaa cagggtcagt ccccgtatct actttgcgaa agcttcgagg        60
cgagcgtgaa gtcaagggct gcggtggatg ggggtaaaan gcctcctcnt cccactgcct       120
gcnccgtctt ggggtaaccc ctanccccca cccggngttn cnctttaatg ctc              173

<210> SEQ ID NO 37
<211> LENGTH: 369
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 37
tcactgtgcc gggtctctcc tncccggtcc aactccctta cttgtcctca tctctgtccc        60
caaggtccgt gacccgcgga ggtgatgggg gggataggag agcccagggg accgcagagg       120
tgacacaatc gcccgcccgt cctccctcgc tgggagccga ttcagcctgt gccgagcctc       180
tcccttcgcg tgcctctgcg cacagcggtg gcaccgcagg actccgggtc ccccccggct       240
ctccatcggg aagccggcaa atgcgcttcc tcagccagac cgcggcgggg tggggcggg       300 ggggcggaa gttgaaatac tgggacagaa acacctgccc gtcccaaggg acggaaaact       360
ggatgccaa                                                                369
```

-continued

```
<210> SEQ ID NO 38
<211> LENGTH: 123
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 38
gtcccttcgc ccgctttttn ctttccccna ggtcccagcg nccgaaccgg cggatgtcca      60
cgaaacatag ggcgagccgg gggccangcg gggccgtgta aaatctcntg tggtcatttt     120
gtg                                                                  123

<210> SEQ ID NO 39
<211> LENGTH: 450
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 39
ctagccctgg aagagaatcc gaggctcagc cntgctgcag cacccaggac actgcatccc      60
agcacctgcc cgaagatcag cccaggaccc aaaggaaagc aggctccaag ctccccggaa     120
gccaaggaaa ataggaaaac atatcctgcc ccggggacac cttctggaac tatgaccaca     180
tgcacttgac cttccggaac aatcaccgca tgcacctgac ctcccggaac tgtcaccacc     240
gcgcgcacct gacctcccgg cactgtcacg accgcgcgca cctgacctcc cggcactgtc     300
atcaccgcgc gcacctcacc tcccggaact gtcaccaccg cgcgcacctg acctcccggc     360
actgtcacga ccgcgcgcac ctgacctccc ggaactgtca tcaccaggcg cacctgaccc     420
cccggcactg tcacgaccgc gcgcacctca                                     450

<210> SEQ ID NO 40
<211> LENGTH: 593
<212> TYPE: DNA
<213> ORGANISM: Homo sapiens

<400> SEQUENCE: 40
ggaccaagct gggtaaactg ccgacagctc cattgggcag catgtccacc cctgatgacc      60
aaatcccacc aaacgtgcag ctggcactcg gccgcctttg tttccttccc ctagaataaa     120
actccgctgc tttcccacgt tcctggagca gcagccggaa taaagcgccc atggccttgc     180
cctttgagtc tcggaggatg tttgccactc aacaatgga cttttaaata attcaggggt     240
caaaaggcgt gtgtgtgggg gggagaaaa gttacaaatc agcacttgaa accgaacaca     300
aacaaaaatc aaacaaatcc gaactaatat aacaaatcaa aactttgatc tttagaagaa     360
aacttcaacc ttaatgcttc caggaggaaa gcagaaagga taatgactga attgtgaaaa     420
cgagccaaaa tgttccacca ctgatgtcac acacacctat gactccctgc acagatccac     480
ggtcccgggc gctgaatccc cgcaacccte tgcgcccaca gaggttaaac tctcgctgct     540
ggcgacttcc gcttcctggc ctaaatctga cacgcacgac tcccccgcg gca            593

<210> SEQ ID NO 41
<211> LENGTH: 457
<212> TYPE: DNA
<213> ORGANISM: Homo sapiens
```

```
<400> SEQUENCE: 41
accaccaacc aaatagggcc tttcctgtta acgaccacgc ggcaaggggg ccgggccctc    60
gcacgcctcg acggcctccc ccactccaaa gggactccga tttcgcagga tctcccgcct   120
cccgcctctg ctcccaacac cctacgtttt tctcttcctc ctcatttacg tatttacaat   180
aaaacagcga agctgcacag tctgtctcta aatcaaacgc ggttaccatc aaagcctcag   240
actctatgtc tcaaccgcaa aaggtctgac aggaaatcaa ctcgggagtt tgtcaattct   300
ttaaactcaa agctctgtta acgaaatctg gatctttcct cgctccccac ctgcctcccc   360
tgacaggaga atgactgtaa aaggatcctg tcgtccccga agtcagcac caagcacttc    420 acaaattgtc aaatctcaaa agcttacacg cgcggca                            457

<210> SEQ ID NO 42
<211> LENGTH: 211
<212> TYPE: DNA
<213> ORGANISM: Homo sapiens

<400> SEQUENCE: 42
gcctgacctg aatgacgcgc atgttgaggc cggtctcctg cgccagctgc tcgcggatgt    60
ggcgggtggg cttgggtgta gcagcgaagg cggccttcag cgtctccagc tgcttggctt   120
tgatggtggt gcgcggtccc cgccgcttgg cgcccaggtt ctggtcgtca ttctcgttgc   180
tacccgcttc cttgtccgac acgtcggcgc a                                  211

<210> SEQ ID NO 43
<211> LENGTH: 141
<212> TYPE: DNA
<213> ORGANISM: Homo sapiens

<400> SEQUENCE: 43
aaatcatctc cgggggccca gcacggacac gctccagacc cgtgagttcc ccagcgccgt    60
gccgggaggt cagggcgct gaaagaagga agaattcagc cacctctcag catccctgtt   120
acctcgagga cgcgcctctc a                                             141

<210> SEQ ID NO 44
<211> LENGTH: 559
<212> TYPE: DNA
<213> ORGANISM: Homo sapiens

<400> SEQUENCE: 44
acccactttc cattaacact aaataaaacg catccatgga tttcctctcc attccgaggc    60
aacaggagtg catggcacat tgccctactc ccctgaagct cttcgctaac ctaagactcc   120
agggtgagga agttagctgg agcttttttaa agtgcatctc caaagagaat tttgctcaca   180
ccatgagagc ccccaagaaa caccagggcc cccttagatg ccggagacca cgccctccag   240
gaataagccg cacccctctgc ccagcagatc cttgcgcgag tagcccctctt tccctggggc   300 taatcaagtg catgccacat gtcaccactc tcagctggca attcttcctc agaggcgcag   360
actttcacgg aatccccagc aggggggtt aagagattca ggggaggccc cgcccgtgcc    420
ttccacaaaa gtcgctttac cgtggctcgt gtcctgcggc cccaagggg tagcctggga    480 cgtgtattgg gagggcatag aggctccttc caggacaagc tgccagcctc cagtgggcaa   540
ccatgtgaga ggcaaaatt                                                559
```

<210> SEQ ID NO 45
<211> LENGTH: 433
<212> TYPE: DNA
<213> ORGANISM: Homo sapiens

<400> SEQUENCE: 45

```
gcgaacagca caaaggcttc attcctacga gagattaagt tttagagcaa atggacacga      60
tcgttaaaga atttgatatt tccatgtaaa ctgcattagc aggttatgcg atccaaactc     120
acaggaacaa ctccaactct cggccatgcc ctatttcatg tctagatttg tttaaccgac     180
ttacatcata atccaagaat acgaactaca gtatattctt acagcaaagt tattccttaa     240
aagcaaaacc gagccacctt tgaaaacacg cacacacatt atccacggca ctaaaacccc     300
agtcttgacc gagaaagacc aacaacttgg gggggaagaa aacaacttca gagccagagc     360
tcccaaagca gaaagcgctg gcggctgaag ggcacacgag gttccgctcc cgggcgaacg     420
ggcggcgtcg caa                                                        433
```

<210> SEQ ID NO 46
<211> LENGTH: 487
<212> TYPE: DNA
<213> ORGANISM: Homo sapiens

<400> SEQUENCE: 46

```
cccttagtat tccatgagcc accattttcc ccacgatccc tccagcctga acgatcacat      60
cctactgtgg accacgactc tcccagcagc gggcgtttaa tatccagtta gcaggttctc     120
accacccct cgctggctcg aatacagcat ctgcaccgag ttcccgagaa tcgtcaaccc      180
agcaaatccc ttaattggtg gacatgaaaa tccagggctt tgtgctgtaa taacagagtc     240
ctgggggcct ggggagtttg tgccgcttgg agctcaggtt tctgggacag aggctgagcg     300
cagggcaggg aggcaggtct cacctggcac ctcccagagt cctcgccgag cagatggaag     360
cagaggctct cgcgcccggc cccgccggg agacctctct ctctttccct cggcctgctc     420
tgccctctcc cgccttctcc ctgtctgatc cttctctgct gtcatgttct ttgtcctcgc     480
gccccga                                                              487
```

<210> SEQ ID NO 47
<211> LENGTH: 403
<212> TYPE: DNA
<213> ORGANISM: Homo sapiens

<400> SEQUENCE: 47

```
gtcatataag cacaaccatt cccagggcca ccctggatgc atcagatcag tccccccact      60
ggtgaccaca atggctggct cagagtgcct ttgaacagac aggagaaaca gacttcttgg     120
agggagggac cttcccacag ggaatggcca aggagctagg tcttcagggc ttgcatggcg     180
tggagtgtgt gctcaggtgc acagtgaagc aaacctgagg ggacttgggc cctgcgtcct     240
ccagcacaca cgcaccctt cgccgtcaca tccggggcac ccacccgtgg aatatgtgag      300
ccgcacttgg ccagccacga gttccagggc caggaagtcg tgcttctcgt tcaggcgccc     360
gttgtagaag agcagcccgc tctgctgcac tgtcgcgtcc cga                       403
```

<210> SEQ ID NO 48
<211> LENGTH: 155
<212> TYPE: DNA
<213> ORGANISM: Homo sapiens

```
<400> SEQUENCE: 48
ggcgtggaga ggaggggca gaaactcagc cgccctacg tttgctaaac tgcgtccgcc      60 aggggcgta tttttctaaa acgcacaaga cgtttcgtgg gttatcgatg gtctcttgag    120
cctccttgac tgatggggat tgaccgggcg ggata                              155

<210> SEQ ID NO 49
<211> LENGTH: 256
<212> TYPE: DNA
<213> ORGANISM: Homo sapiens

<400> SEQUENCE: 49
tctactgagc ttttctttaa gtggaaccag aagtgctggg atgagaggga aaggatggga    60
gtgcgtccaa aggtggacag caggtcccca tccctggtgg gagtgagact ggacggcatc   120
ccccggaaag gtggtttggg ccttggacaa ggctagaggc aggagtccat gatgcagaga   180
tgacacagtg cccctccgcg tgtgagtcca cgaaggtcac tactgaggct ttgtgcttgt   240
aaaaggccgc cccgca                                                   256

<210> SEQ ID NO 50
<211> LENGTH: 224
<212> TYPE: DNA
<213> ORGANISM: Homo sapiens

<400> SEQUENCE: 50
tgcggggtcg tgggggaacc ggcgggagct gttcgctggc cggcctcact ggagtaggaa    60
ttttagatga aactgagtcc gtttctcctt gaaggcaggc agtattctta gatctactat   120
tcatttaaaa agaaggaaaa gaaaaaaaaa tgactgctac ttactgagaa gaaaatttct   180
gttctcctcc gattccgctg atcccgcttt atccgcgcac ctca                    224

<210> SEQ ID NO 51
<211> LENGTH: 313
<212> TYPE: DNA
<213> ORGANISM: Homo sapiens

<400> SEQUENCE: 51
gtggctggga cggcccaggc cgcggcttcc cgcgtgggga tgcgctgtgg cgcagagctg    60
gtcccggcgg ggccaggcgt ttgtgggcgg gtgacgggga tctagggctt ccgctcgtga   120
ttcctcttgg gctgtctttc cgggtttgga ctcgcctgcc cggctgtgtg cagggttccc   180
gctgcctctg gccggcaggc gtccgggctg caggtgggcc ggcaggcagg tgttagcggg   240
aagggagcac aggtagcgag gtgggatcgg cgacctggct agggtgtcgg cagaatggaa   300
tgcgcggccg cta                                                      313

<210> SEQ ID NO 52
<211> LENGTH: 385
<212> TYPE: DNA
<213> ORGANISM: Homo sapiens

<400> SEQUENCE: 52
tacgttgcgc attcattctg ccgacaccct agccggtcgc cgatgccacc tcgctacctg    60
tgctcccttc ccgctaacac ctgcctgccg gcccacctgc agcccggacg cctgccggcc   120
agaggcagcg ggaaccctgc acacagccgg gcaggcgagt ccaaacccgg aaagacagcc   180
caagaggaat cacagcggga agccctagat ccccgtcacc cgcccacaaa cgcctggccc   240
cgccgggacc agctctgcgc cacagcgcat ccccacgcgg gaagccgcgg cctgggccgt   300
```

```
cccagccaca cccagcgcgc cttctccagg gtcagccagc tgcggctctg ccgaagcgct      360
cctccgctcc tttctcgcgc cccga                                            385

<210> SEQ ID NO 53
<211> LENGTH: 307
<212> TYPE: DNA
<213> ORGANISM: Homo sapiens

<400> SEQUENCE: 53
aacccggctc ggttcggcaa ggttcaggga gacaaggtag agaaggctgg ggtgagcaag      60
aagtcgggcg gccgatcgtc agggccacga gcctcgcctt gccttcttgg aatcccaccc     120
aactttaaag gcccaaagat cctgaaaatt ccgaaagcga aactgcgggc tggtctccag     180
aagtttgaga acggtctccc aggctttcca gcgtcgtccc gggattctcg gacaccacaa     240
acgccatcaa ccacgagcac cggtgtccgt ggctattgcc ccgaatggtc cccatccgcg     300
tccccta                                                               307

<210> SEQ ID NO 54
<211> LENGTH: 182
<212> TYPE: DNA
<213> ORGANISM: Homo sapiens

<400> SEQUENCE: 54
cgatgtcgaa gccgtttgga gggaacagcg gtttccaagt tcctgctgac ttgagaagcc      60
tctgcgggtt tccgaatctc cggcgcactc ctgggcgcgc tgcgggagct gtagctcagc     120
cagccaggga gtagcggctt tcatccgccg ggaggagtct ttcgagttca atcgcggggg     180
ca                                                                    182

<210> SEQ ID NO 55
<211> LENGTH: 523
<212> TYPE: DNA
<213> ORGANISM: Homo sapiens

<400> SEQUENCE: 55
tcgggtttga tccgccccaa ccaaataggg cctttcctgt taacgaccac gcggcaaggg      60
ggccgggccc tcgcacgcct cgacggcctc ccccactcca aagggactcc gatttcgcag     120
gatctcccgc ctcccgcctc tgctcccaac accctacgtt ttttctcttcc tcctcattta    180 cgtatttaca ataaaacagc gaagctgcac agtctgtctc taaatcaaac gcggttacca     240
tcaaagcctc agactctatg tctcaaccgc aaaaggtctg acaggaaatc aactcggag      300 tttgtcaatt ctttaaactc aaagctctgt taacgaaatc tggatccttc ctcgctcccc     360
acctgcctcc cctgacagga gaatgactgt aaaaggatcc tgtcgtcccc gaaagtcagc     420
accaagcact tcacaaattg tcaaatctca aaagcttaca cgcgcgggca ctccggaaag     480
gctgtgggga ccacccaaag cacccccctc cacaccgcgg gca                       523

<210> SEQ ID NO 56
<211> LENGTH: 795
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base
```

<400> SEQUENCE: 56

```
tttactttct tccggctgac gtccatctcc tcaaatttct caggaatgtg gggaagctcc      60
tagccctgcc tgcctttcta gagggcttct tggatttgca gcttctaaca agttgctctc     120
gccacggaga agctgttatt atgacaaaat atttggggca ttatcaaaat cacacaggct     180
gctgggctgc tgtcggtttc tcgccagggc cagtaagcag ttacatttgg agttgctacg     240
tgttgtttgg gggccgggct gtggagagtg actgagccag tatttttcat ccaaaattct     300
gcaaattgaa ttaaccacaa ttctagtctc acctcccgtc tttaaaaaaa taagttgaag     360
aaaaggtaaa tattagagat aaggcagcat ctagtgactg cggagaggca caagctggtg     420
ggcgagggtt gggggagtca gcaaagccct tcaaaacctc cccgtttaat tttctggctg     480
tctctgcatc ctgttgccag aattccaaat gcttggagtc atttanaggt gcagaactc      540
aaacgtcgtt ccacttggaa aggggaccgt ttaacgttaa attccattag cacctaaatt     600
gtttcttaaa gacatccgct cagacacagg actcgaaagc gagcatttca tgcaaataaa     660
tttctcaaat tttaaacctt gttaaaagct tgtctcgcac ctcggctccc tccccttccc     720
cggaaganaa caataggccg ntggcgcatc cccacttcgg antaaatatt gacggggaa      780
gttgctaaaa acatc                                                      795
```

<210> SEQ ID NO 57
<211> LENGTH: 438
<212> TYPE: DNA
<213> ORGANISM: Homo sapiens

<400> SEQUENCE: 57

```
gcctgtgtgt aggggactgg aggtggggga acctgttctt ttcttgtgtc tgatcctggg      60
gctcgcttcc tgggtcctag aacagcagcc aggacggaag aaactgttca cgttgcaccc     120
ctttctctaa gattcccagg ccaagagtag ctgcagaagg tggccctgaa tctatggcct     180
ccttctctct gcctgacccg ctagtggat ccggagaggg gaccagggag agctcctccg     240
agcaggggtc cttcgggaga cagagagggg tccaggctga gagaactctt caagcatggc     300
gagtctgcgt tatagaatcg ggcgggcggc tcaacttggg ggaagcacca agaagagctg     360
ggcgacctgg agcgcagaac cggctttggg gagccacccg gcggggcagg ggtagcacgg     420
agcccgggcc gcggccca                                                   438
```

<210> SEQ ID NO 58
<211> LENGTH: 611
<212> TYPE: DNA
<213> ORGANISM: Homo sapiens

<400> SEQUENCE: 58

```
gcttcccccct tcctttctcc cgcgctgccc ccttgagatc cgaccttcg tgtgtttgcg      60
ctaaattgtc ctcgctgttc ctctcacccg cgacatacag agaaagtaac cggagagccc     120
tacatatgcc agtctggctg ctgccctgga gtttgcatcg atcctgcaat tcctagtcaa     180
atatgaacac tcctctcccct cctcacgccg agttgaaaaa cgtgataata atataagtcg     240
acaggctgta ggcaatattt ttcactgcat gacttattca tggcgaaaat gtaaactgtt     300
ttcccacggg ctttattaga atgttgcctt ctgccgagat aggcttcacg caagccctgt     360
gctctcagtt tctctggcgt gagcaaaact gtttgggtcc ataagtgtcc acatttggcc     420
atttattatt tcgatttgaa ttttcagtaa atacaaccac cccttccccc tccccagaa      480
acagtcatgc ttagagaaaa ttatagcaaa acctccctgg aagcctgaag gttttggatg     540
```

```
actgagaggt ttggtttggt ttctctttct tttcattcaa aacggatcaa actccctggc    600
tcgcgtcccc a                                                         611

<210> SEQ ID NO 59
<211> LENGTH: 291
<212> TYPE: DNA
<213> ORGANISM: Homo sapiens

<400> SEQUENCE: 59
gagtttggca ggccccggat tccacaaagg agtaggcgcg gccagccgcc tccagccctg     60
agctcagtaa attcggtgtc ctgaatgctc ccttcctgtc cttaccactg cgagctctct    120
tgggacagct ttctaggttc cactgcgacc tactttccgc tccctgagtg cttctttgct    180
gaaactgcag gcgaaaagat ctctttccca gaccgcagcg cactttgaga aggggctcaa    240
agtcgcccgc tctgaatccg gcaccggcaa ataggagtag ccgcatgcgc a             291

<210> SEQ ID NO 60
<211> LENGTH: 226
<212> TYPE: DNA
<213> ORGANISM: Homo sapiens

<400> SEQUENCE: 60
gaaaacagat aaaacgccct acagaaaatc tcggcgaagt cccggaggac tctggtttct     60
aagatcagct gggcgcactt tctccgggac gtcccttctt ctcggtctca gcgccttcct    120
gccctcagcc gcgcgcagct ttgttttggt gacaaactga aataagaaat ggaaatatat    180
tggcctttgc tgctgccagg gatgagaggt tgttgacgtc ggcgca                   226

<210> SEQ ID NO 61
<211> LENGTH: 580
<212> TYPE: DNA
<213> ORGANISM: Homo sapiens

<400> SEQUENCE: 61
ctgtgatgca ctcggcggat ctcggtggca gctgcctcct tcatctccag tgacgcctgc     60
atgctgtcct aggcagtgtg aggagtgaag atgagatttg gcgcatcttt caacggagtc    120
tgagcaaagc taaagggctc cgattcgtgc aagccaaggg ctgcccctcc tatcctgtcc    180
tccttgagga cctgtgctaa ggcttttctca tccaccaggc caccatgggc tgcgttcaca    240
aggaatgctc cctgtctcat ctgctttata gtaaagtcat tgacgaggtg gtggttatgt    300
tcattgagat tgctgtgcaa cgagacacag tcactctgat acagcaaacc ctgcaggtg     360 tatcagggtc ccctctgcat gccctgggac ctctctatct tgtcctacaa gtaggggtca    420
taaaatacga cgctgaatcc aaaggccttg gctcaaactg caaccgcctg cctcatgcaa    480
ccgaagccca tgaggcctag cgtcttccac gaatgagggc cactcccatg ccacctcga    540 gaatctgctc cacgctctga acccgcgcac ctcaagccga                          580

<210> SEQ ID NO 62
<211> LENGTH: 633
<212> TYPE: DNA
<213> ORGANISM: Homo sapiens

<400> SEQUENCE: 62
gcccaggaga agccctccac ggtgggcgtc ctcctagaca accagcaccc cctgcaggca     60
ccctcgtctg gcagaatcag cccttttccca cctgcaggcc cttctcagcg cctctgactt    120
cccacacaca gcacaggtta caaactggtc cctggcagtg cactctagcg ggcctctctc    180
```

```
acaagttctg cgggcctcgt ttcatggaaa gcgggttgtg gattcctgct gcccttggat      240
ggcccctgcg cacgcacacc tctgagcggg cactgagcga gcgtggggag ctgctccctg      300
ggaactaggc aggagctttt aaacaccctt acacacagcc attctgcggg aatacatgct      360
ttcccggtaa ggcttttact gttcattcca ggtaaattgg aagtcgcaca ccccaagctc      420
caaatacaac tcgttagctg gcaggtctct gaagccaatt ccttctgagg aaaatggaga      480
taatagcagc tacccctccca ggtgactggg ggagaataaa gtggctgtgc atagtggtgt     540
ttgcagctgg tggctgctat tatccttcat tacagcttgt aaaaagggtg tctaggccat      600
ttacacacag ataggccggg tggggtaagc cga                                    633

<210> SEQ ID NO 63
<211> LENGTH: 703
<212> TYPE: DNA
<213> ORGANISM: Homo sapiens

<400> SEQUENCE: 63
gcctatgaat ggatttataa ttgctttatt tttgtcccat ttagacagaa gtcagagaca       60
gaggagagaa ccaaaaaact tggatgtttc cgtaaactag attcgtcaat cctcgataat      120
tgaaagtagt tccagtatgt cagccaccgg ggttccctgg ggagctaacc agtcctgaag      180
gaagtatgaa gaggaagagg aggtcttcag ttaaggggat gaatttgtgc agtcctaagc      240
cctgcaaagg tgctggaggg aggaagaagg gcaggaaata aagatggaa  gaaaatttgt      300 tttttatcca cttagagttt tatctttaat gatgggaaac agtgctgctc tcaggaaact      360
cagtgtggag atctaggagt tcacggttca tagtccatta ggagcaggaa aaggatagag      420
gacatttata aagtaacatc caagtccaaa gtaaaatggt ataaattgtt tcccatgata      480
aaggctggct gagtaggtca ggaaaggtct tgtcagacca tatgtgctgt ttcaggctgc      540
ttcaaattct tttaggacag tggtggatat gagtgaagac ggggcaggca ggccacatct      600
cttagaagag gaaggtgatt gccacgtctc cttcctccat gctgatggca aggcgtgcgg      660
gctgtgttct cttgcagcca gcgtcccatg ctcggcggcc aaa                         703

<210> SEQ ID NO 64
<211> LENGTH: 420
<212> TYPE: DNA
<213> ORGANISM: Homo sapiens

<400> SEQUENCE: 64
gtgacgtgcg gaatacacgt gatgtcgggg acaggagcgg gctgaagagg gcacgatccc       60
acgcggaggc caccctcac ccggggtagg agcccgctgc acttgctgtc gctcagcccg       120
ggcgctgcac cacggcagcc gccatgctgc ttaaagccgg tcatgtgacg cgggagccag      180
ggtggaaggg gtccccgcgg gcaagccttc gacacgtgac ctgccacccg actacggaag      240
cctcttgggc gttccgcccg ggctcacatg tcatgtgacg gccggccggt cgccggagta      300
accaggaact ttcccagacc ctgccggtccc tggagcgtca aaagagcgt ccccgtgact      360 aggtggagtc gcctgccctt ccgaatctca gctgtcttat ctggaacccc cacgcggcaa      420

<210> SEQ ID NO 65
<211> LENGTH: 496
<212> TYPE: DNA
<213> ORGANISM: Homo sapiens
```

```
<400> SEQUENCE: 65
gcgctgcacc aatttagagg gtagaaaaag gagttagaag caaagaggaa aaaataaata      60
aacaggcaac aaaaacccaa cccagccagc ctgagccatt tgcattagtg ttcatttagg     120
aaattagcag acgggaaacg ctggggagtg gagtgggccc cggccttggg gactgcagag     180
cccgctcagc cctgggtggc tgggcccaca tggctgtcgc caggagcaca ggaggaccca     240
gaggtggccg agggagcctc gccgggctcc ggtatgggtc ctggcccctc acaggtgcga     300
gcctggccca gtgactgtgg acgctgtggg agagcaggcc tccgatacgc agggctggga     360
ctgctgacct ggaaggtggt gccgggcgtg tctggtgaag gcgccgttgg cagctagaga     420
gagacggcgg atgggtgac gccataaccc acggtcccag ttttgaggct tgacggtgac     480
ggaaaaggac gtcggc                                                    496

<210> SEQ ID NO 66
<211> LENGTH: 637
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 66
cgccgagccg ggatgagcaa ggcttcctgg aggagagggc cggcctgagc ttggaaggat      60
ggggaggagc cactggctac aagggtgtag aggtgagaac cagtgtgacc tgcccatcgc     120
tggtcgtctc tgggtcattc agctgaaatg gcatctctga gctgagagga gtgttgcctg     180
taaggagcta ggcatcagcc cccagtagag gggcggccca ggcacagccc atagccgcag     240
acttagtgag tctagctagg gagacagtag aggggccaaa atgaggacac aggtcaccaa     300
aaatcctggc caggtcctgc cactacctgg ctcagcgacc tgccccccg agcctcagtt      360 tcccccattg gtggaatgga gtgaggaaga cgcgcctccc ggggctgcga tggagaattg     420
agtcagagtc tgggggtgct gggagggctg gggagcagcc tccctgagcc tcagtttccc     480
tggctgggga atgaggacct tgctcgtccc ccctcataag gggaagctgt caggaaagtg     540 cttttcaacgc tgagccattt cccagtggtg cacaattagc tttccagagg attttggtgg     600
attctagagc tngagggctg ggggatnggc ggccaaa                              637

<210> SEQ ID NO 67
<211> LENGTH: 595
<212> TYPE: DNA
<213> ORGANISM: Homo sapiens

<400> SEQUENCE: 67
gccctgagct cttgagggcc tctgcagttc ttgggacaat tctgggacta tatctttggg      60
ccttggtgag atctagaggc tctaaagtct ttggagggg tcctgagctc cgtgacggc      120 agggtcttgg gcactcactt gcattcttga ggggtgtgtt tggcctcgtc cgtgcaggtg     180
tagaatttcc cctgtagaga ggatgtctgt caagtaggtt caccctcat cacactcccg      240 cccagacccc tgcctggcat tccctccagt gtttgcccca ccttgaagag ctgcaccccg     300
atgcaggcga acataaattg cagaagtgtg gtgacaatca tgatgtttcc gatggtccgg     360
atggccacaa atacacactg cacccacatgc tgcgggcacc caagcatatg gctactgaac     420
actacaggcc acagtggtca tggggcaggg actctggtca tagatgcagc tgagggactt     480
```

```
gggctgggga catgtggtga tgggtcaggg atgtatggtt agcaacatgt gttcaagagg    540
cagtgttatg ggctagagac gtgtgggcat ccaccaggaa taagtgtttg ccggg         595
```

<210> SEQ ID NO 68
<211> LENGTH: 580
<212> TYPE: DNA
<213> ORGANISM: Homo sapiens

<400> SEQUENCE: 68

```
gagtcaggac ggaggacgcg gcaggtcaca gagcccacca agtccgaagc tggaagttca     60
gattctttga tattcaaagg tggatcatct gtgcttttt ttttttatca gtctctcact    120
ttttatccat catctaattg tgacagctta tttgccttta taccataaga tggggagtag   180
ggttgagatg aaatccaagc atcgtttccc ttccccgatg gtcgcctccc tggggtgaga   240
cgttcgacgt gtcagacttc accaagagca tctcccgcct cggtgcagta atgaacttgg   300
aaacgattta ctccggcact tggttcctgt ctccataaat gcggctgctt taagggaat   360 gtaaaaggg ctgtaaattg gtattgattg ccggtggtct tgaagaaccc caactgagga   420
ttgaccgttc cttggagtga aggctccgca ttcagacgcc tttcgcctta cgtcatcata   480
attgagaagg gaaaggagac gtgttagttt cagtctgatt atttaccatc aaggcataaa   540
cacttctcag aggcagcgga acccattaaa ccggcccgta                          580
```

<210> SEQ ID NO 69
<211> LENGTH: 589
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 69

```
acacgggggg caacctcttg cacctggctc cctgccctcg gtgccacgtt tccagggttc     60
ctccacgtcg caggctgtgt cagcctcgct ccttccactg cagaattgcg gtccacagcc   120
tggatgggcc actctccatg tatccacctg tccctccgtg gctgctgggc tgagtcgctt   180
ctgatgctaa caagaggcgt ccggctggac taaggcccccg gaagctgaga actggagggc   240
aggtgcgggc atcgggcaga gcagctccag caggcaggac ctggggcctc caccctgcac   300
ccctgtgccc cgcgtgtggc ggaaccgccc cgaggggagg ctgtcaccac ggtgacaggc   360
agccccacgc gagcctgaga accctcagcc cacctttttc tgtaatcaca gcaggcatct   420
ctccggcaag tcaatccagt tccagctggt gctgcctccc ttgcctcatg ggctttattt   480
tagaactctg agcaataata aaaaagacgc tacccgctac aatagatgtg gcagagaatc   540
tggctcttca cttcatcana gatcaccctg aaatgatggt tgttgttaa                589
```

<210> SEQ ID NO 70
<211> LENGTH: 748
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 70

```
gctacatctn ctctacattc taactaacac ttgttatttt ctgttttgt ttgtttgttt     60 ttaatagcca ttctagtagg catgaagtgg tgtttgcctg cttttttga tggaggtgga   120
```

-continued

```
ggaatagggt ggaattggtc cttaaccatc aattaagctg ggggccttag acctctgtga      180
attggctgtg acaatagcta aaggaggctg ctacctcata ctgaagagat gtttcctaag      240
tttgtcaccg gagagggcac cgaaccaact tattgtcttg gagggaagaa gcagcaaggc      300
agaagacttg aacttctcag agaaaaaaac agtctacaga cttcatttta tgctgtcctc      360
acacactact gaaagctcta ccctggggac ctggcttgac ttctaaccta cncctgtgtt      420
atttaggaag agctcccagc tgctctgagt ctcagtctcc caatcagtga aatggaggca      480
atagcacctg cctggctgca tcgcccaca gtgctgcaat gagcatccaa cgagagaaag       540
cttgtcacct gtgttgcaaa ctaagttaca caaatgcagg cagtagcagc tagaagaaaa      600
tggttgggaa tctgaaaaga attaaagccc cccatgaatt tcttctcacg cctcctccaa      660
aagccaggga ctgcttcacc ccgcctccag gactgctcgc tccagcattt ccggcagctg      720
ctgacagaat gtatgttgcg gctgtccc                                          748
```

<210> SEQ ID NO 71
<211> LENGTH: 599
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 71

```
gatgactgtt gcccgagctg aggccacgac ccaaccccga ggaagggaga acagcttccc       60
atgaagggca tggctgctgc cccataatcc cagggcagga aataaaggga tcttggacta      120
ggcaatcaaa ggacttcctc tccctctaag gccaaggagg aaatgtggct gggactccaa      180
gctctgtgga tgcctggagg tgccagcagc tggggatcag ctggcccac ctgcagagcc       240 agccagtggt ccccctgcat ctccaaggtt gggtctatgg gctccaagaa caggtgtttc      300
tcagggtaac ctcagcccct acaacttcaa ccaagagagt gaagggagc agccctggag       360 gccaatgagg aggggattga tgtggtcactg atgacaaaga catccctgtc cccagagcca     420
gccccttgtg agcagaagaa tggctgccgg gcaaaaggac ctgctatgcc ctccccatac      480
acatatcatg ncacctgggg accctctgaa taacaggggg cngctttaga gtggcttnat      540
taccaacaag aggcccagaa gggctagagc acacgatttc atgntcggcc gcatgncaa      599
```

<210> SEQ ID NO 72
<211> LENGTH: 614
<212> TYPE: DNA
<213> ORGANISM: Homo sapiens

<400> SEQUENCE: 72

```
gtgcgctatc acgactgttg cccgagctga ggccagaccc aaccccgagg aagggagaac       60
agcttcccat gaagggcatg gctgctgcca ccataatccc agggcaggaa ataaagggat      120
cttggactag gcaatcaaag gacttcctct ccctctaagg ccaaggagga aatgtggctg      180
ggactccaag ctctgtggat gcctggaggt gccagcagct ggggatcagc tggcccacc       240 tgcagagccc agccagtggc tcccctgca tctccaaggt tgggtctatg gctccaaga       300 acaggtgttt ctcagggtaa cctcagcccc tacaacttca accaagagag tgaagggag       360 cagccctgga ggccaatgag gaggggattg agtggtcact gatgacaaag catccctgt       420 ccccagagcc agcccttgt gagcagaaga atggctgccg ggcaaaagg acctgctatg       480 ccctccccat acacatatca tggcagctgg ggagccctct gaataacagg gggcgcttta     540
```

```
gagtggcttc attaccaaca agaggcccag aagggctag agccacacga tttcatggtc      600
ggccgcatgc gcaa                                                       614

<210> SEQ ID NO 73
<211> LENGTH: 552
<212> TYPE: DNA
<213> ORGANISM: Homo sapiens

<400> SEQUENCE: 73
aagcgcccac agatggccaa gcatgtggag gagagcacaa tattttattt aaatatccaa      60
atacgaacac attcccgcat ggcaccaaca gccgcctgaa cacgcccgat gccggcttgt     120 gcttttccg ttttgtctag aaatttgggt tgcactaaat tctcagctga atgaagatga     180
gaaggggctg gcagaggggg tggctccagc tctctgagaa cctggctcct tcccgggtgg     240
cagggagaga tggcccctgg ggagacgggg agggtgcact gcctcatgcc caaccacca     300 gcttctagtt gagaaatcag aattttctct gcagaataag gaaaaagcat tgtcaccatg     360
attcacgtgg agctggccac actcaggaaa ttcaatgggg tcccacaggg gctccgaggg     420
ggaaggagag ggcctgggac atgcccctcc agccatcatg gaacaggatg gcagggccg     480 gccctcactg ctctctaaca gtgaaaagcc acatctccac tttggaaaac acaggcatgt     540
gagagcctgg gg                                                        552

<210> SEQ ID NO 74
<211> LENGTH: 450
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 74
tggaggcttc gagggaagtg aggttccctc ggacacccta gtgggaaggc tccacgcggt      60
aatggaacca cgctgtgaaa cctttgcctt tgggtgtcat ggtggaagca atcttagaa     120 gacatttaat ttaaaaaatt cagttttaaa aaatgttgac ttaaaaagca gttttgaaaa     180
acaacctgga attagcctga gatcgatgcc aactcttagc agtctgtata ctaaacacag     240
ttaaacaact gtagctgctg gcaagctgga acctttttgt aaagaagcac ataaaaagga     300
cagaactggt ggaaggtgca ctggtctttc cacatcgcca ccaggcgttt tgaagcgtgc     360
tgctgacacg ctactcanat gcttctgaaa gccaaacaat aanaaaaanc cccattgttt     420
cccttgctgg gttttacccn ccatggtgga                                     450

<210> SEQ ID NO 75
<211> LENGTH: 432
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 75
ggacaatgag gaggggtgc acgtggaatc cccacggata ggccggacgc cgggcaggag      60
cctttgcagg ggtgcacagc ctcctctgga agccctggtc gctgcctggt gcctgctgca     120
ccctgcgggc tccgcagcgg tggagccagg cctgaactgc ctgctcttgg ccccgcctgc     180
ggccctctgc cctttgtctt gccgtggg cccggggcct caagctggcc cggggttcct     240
```

```
gaagttagct gacgatgggc tggcctctgg ggctgggtcg tgggccttgt gcactggccg    300
ccacgtcacc agcgccaggc ctacccgcgg tgctgctgga gacgcgggat gcccgggctc    360
gggctgtgct ggatcccctg gcgctgcgaa ccccgtaccc ctttccaatc gcgggcncgg    420
nttaaagccc ga                                                         432

<210> SEQ ID NO 76
<211> LENGTH: 501
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 76
gacgagacct agccggcncc atgcgcgcct tgagcctggc gaacagttcg gctggcgcga     60
cgcgcctgat gctcttcgtc cagatcatcc tgatcgacta gaccggcttc catccgagta    120
cgtgctcgct cgatgcgatg tttcgcttgg tggcgaatgg gcaggtagcc ggatcaagcg    180
tatcgagccg cccgattgca tcagccatga tggatacttt ctcggcagga gcaaggtggg    240
atgacaggag atcctgcccc ggcacttcgc ccaatagcag ccagtccctt cccgcttcag    300
tgacaacgtc gagcacagct gcccaaggaa cgcccgtcgt ggccagccac gatagccgcg    360
ctgcctcgtc ctgcagttca ttcagggcac cggacaggtc ggtcttgaca aaaagaaccg    420 ggcgccctg ccgttgacag ccggaacacg gcggcatcag agcagccgat tgtctcgttg    480
tgcccagtca tagccgaatt c                                              501

<210> SEQ ID NO 77
<211> LENGTH: 826
<212> TYPE: DNA
<213> ORGANISM: Homo sapiens

<400> SEQUENCE: 77
gcgccctgtg gggatgacgc accatcctgt ttgtttgcac caagtcattt atctcgtgca     60
ccccaggggg ccgtggtccc tgccgggcca tcatgtctgc ttcccttatt tgggttttct    120
gccccctcac ttcatttctc acttcgcttt tcctccttat ccctttgcag tcttgctttt    180 ggggggcattg ctcagccagt aatttgaggg acacctcgtg gagccctagt gtggagccgt    240
cagagcctgg gtaggattct ccgtggtgag gtgctcaggg agacacagga gcattccggc    300
gcctgttcct tgtgcacatc cgcaagtgtc tgcagtgaga ggcatgggtc ccatcttgaa    360
tgccaacaat gtggcaccca caccccactt gatgggccg agccacagct ggccaggttg    420
accaccatgg acgtgccaga ggcatccgaa acccagctct tgcccagctg ttccactgcc    480
aactccagcg ttagcaaagc agctctccct tgctttgtct tctacagcag agaacagatt    540
aaaagagaag ctgcaggcag agaaatgcct cttggagcca gatgcccccaa aggatctctt    600 tgaacaaagg gttgctcagg tcagcgttag ttcctggcat caagcaacaa atcagagat    660 gctaacagtt ctcagattca ctccaagtga agactcaaag ctggatttat aaatccccac    720
agagccgctg tgcagaggta gagggccggt ttcaggatga ggaagccctc ttggaagcac    780
cgtcctccgg ctaacaagcc tccaacctac tgtcggcagg gagaac                   826

<210> SEQ ID NO 78
<211> LENGTH: 433
<212> TYPE: DNA
<213> ORGANISM: Homo sapiens
```

```
<220> FEATURE:
<221> NAME/KEY: misc_feature
<222> LOCATION: ()..()
<223> OTHER INFORMATION: "n" refers to an undetermined base

<400> SEQUENCE: 78
tgcgcagctc cgcgangtgc ccggcgggcc cgaccctcag actcgcttgt ccctggagac    60
caaccctagc gaccaggctc tgccggatcc cgtcgggttt caactcctat tccgaaggtc   120
ctttctcccc taatcacaac acccactcgc ctcttttttcc tcctcttcct cagcttccac   180
cgccgaccgg gcagccccag ttacccgata acggctccca aggccccgtg tttacattct   240
ttcccactgg aagcagaaat tatcacgccc aaattcctac ctgccttccc tggattcctg   300
gtttcctaag aaacgggttt ggcccacccc tgggcgttcg aacagtccac agaagcgggc   360
aaaggaaaga cgactcagtc tttcccctcc gccaatctct tctccgggac cacagatccc   420
agaagtcacc gcg                                                      433

<210> SEQ ID NO 79
<211> LENGTH: 424
<212> TYPE: DNA
<213> ORGANISM: Homo sapiens

<400> SEQUENCE: 79
ggcgggcccg accctcagac tcgcttgtcc ctggagacca accctagcga ccaggctctg    60
ccggatcccg tcgggtttca actcctattc gaaggtcctt ctcccctaat cacaacac   120 ccactcgcct cttttttcctc ctcttcctca gcttccaccg ccgaccgggc agccccagtt   180
acccgataac ggctcccaag gccccgtgtt tacattcttt cccactggaa gcagaaatta   240
tcacgcccaa attcctacct gccttcctg gattcctggt ttcctaagaa acgggtttgg   300 cccaccctg ggcgttcgaa cagtccacag aagcgggcaa aggaaagacg actcagtctt   360 tccctccgc caatctcttc tccgggacca caaatcccag aagtcaccgc ggccgctaag   420
ccga                                                                424

<210> SEQ ID NO 80
<211> LENGTH: 285
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 80
caaccggggg gcanaggcga tcaaaantgg ggtgcgctgt ggtgggcgac acgtgtggcg    60
cgggtctcat tatccgccct tttcacttcc tggactggaa atggcagacc atatgatggc   120
aatgaaccac gggcgcttcc ccgacggcac caatgggctg caccatcacc ctgcccaccg   180
catgggcatg gggcagttcc cgagcccca tcaccaccag cagcagcagc cccagcacgc   240
cttcaacgcc ctaatgggcg agcacataca ctacggcgcg ggcaa                  285

<210> SEQ ID NO 81
<211> LENGTH: 401
<212> TYPE: DNA
<213> ORGANISM: Homo sapiens
```

<400> SEQUENCE: 81

```
cagatatgta tcctcctctt tccaaccctg cgtccctttg aggcctggtc ggcgttccca    60
acctgcccct accccaccaa ccctgtccc tttggccatt agtcccggat tatctagcga   120
tgccccgtgt accgtctggc tttgctgttt actccgcgct cggccagttg aggccttttg   180
tatttattcc tgattttctc ataggggtaa agtgccttcg ggaggatagg acaagtccca   240
tcctgttcat acgaattaca gctcggactt cgggcccttt tacactgcct tttgtatctg   300
ttaacttgcg ctaaaaacga ttcggttctt ttttttgagg aaggggggttg gggggcggag   360
actctgtcgc ccagtcctga gggccgcggc gcgcaagccg a                       401
```

<210> SEQ ID NO 82
<211> LENGTH: 268
<212> TYPE: DNA
<213> ORGANISM: Homo sapiens

<400> SEQUENCE: 82

```
atagcgcgca caactgtgtc tcttacccag gcacatgcac tatccctgat cccggtgcat    60
gatgggaatg tagtcctgca gccctgtgac caaagggctg ggagtgttta tgagacagca   120
tctctcagca agcaaagcaa ggcctgcaca gccccgcctt ttcctccagt gaggcgcact   180
gttcattaag gagtgttcat gagattacat tttccatcaa gcccagccag tcacgcacag   240
ctctacctct tcctctgccg ccccgcaa                                      268
```

<210> SEQ ID NO 83
<211> LENGTH: 989
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 83

```
gggtaatggg ggtgaacaga gagggatgcc gaggccagct tgtagtgtgg ctgttggtct    60
tgtccatcct atggcacaac cctgtcacca cccagatttt gttaggagtc ctcccccaac   120
ttgagagtgg aagctccttt ggcacaaaaa ggggttctgc atcatccccc agccccagc   180
cctgagcctg ggtctggctc tgaactagac ctccatgaat gaatgcacag catcagtggg   240
gatccaccat catggggaaa tagtagatac aggaatgatt ttccaaccag attacagact   300
atttcaagcc cagccagagc ctaccaggcc aacattcccc aggcttgtgc ctctccgagc   360
ctcagattgc tcatccttca aacgagggac agctctgctg cattacctg aactctaggg   420
tcctttataa gctcagactc cagcttagag cacacattga gaggctgctg caccccagag   480
ccacatacgt gcaacagagg gtggtccaga ccccttattg gtccccatgg ggtttgagag   540
agaagcctcc agaccagctc aacttctccc tcatctcact taggcctttg cacccagctc   600
ttaggaggtt gtcaggtcac agtgccccat ttcttttctc ttccccagaa atcatgcggg   660
ggatacctgc tcagacagga ccttcatgaa agccaggctg tgaggtgtgt tggggaatgc   720
ataattgata ggccatcgtt cggaggccct cctggaggac caaaatgtaa tcagcagtgg   780
cgagcttgtt cacgcagga attcctttta catcctggtg aggccaaaga cctggcaagc   840
aagtccctct ggtcattaaa gaagcatcct gacttgangc aggncacctt aggtcactgc   900
agccacaaaa atctttgntg ctggattcna aagtaggcat tggggctggg atctgggctc   960
tggcatcctt gancgtgtcg ggggccaaa                                     989
```

```
<210> SEQ ID NO 84
<211> LENGTH: 250
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 84
cgggctcgaa acttcgaaga ccgcggaacc cgaagcngcn cttggctcna atcgcttcgg      60
ctcgaggcgc ccgtncgggt cacgtgaggt ggggcgggc cgaagagggg ggctcccctc     120
ctcctgccgc agggttggcc gcaagtgcgc ttcaagaggc gcttgatgac ggttaatgtt    180
gcagcccgga agatgacttt tttctcctcc ttgggttgcg gcaggccgtt agtgggaggt    240
cgcgtcccga                                                           250

<210> SEQ ID NO 85
<211> LENGTH: 402
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 85
ttctcccttg tcatccccctt accagagcca cagaaattat ccctgtgggc tcccttgtcc    60
tcactcggcc ttttctggag ttaagagatc caagccaact actgggtctg ttccctgcta   120
aaatcttagg ccggcgtccc atccacccat ccccatgcct aggacttttta agctggcaac   180 ggtacctggg tttagttttc ccttcgtata tcactatctt cgtngcttac cttcttgtgc   240
ctaaagttcc accgatgtgc aaggngatta accactaaag tgcacctgac actactcttg   300
acaaattgca gttgggaggt gagttgatga ctggccggta aatcaaaagt gcttatttag   360
ggagtgaggg ggcccgcggc anaagccgan ttccagcaca ct                      402

<210> SEQ ID NO 86
<211> LENGTH: 595
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 86
gatcccagaa ggttctggag ccgagtatca gagtttgagc agcgagtcca gcctagcaga    60
agcgggtgtt gaccggagac ttttcaatgg tgcaaaatga cacactgctt ttgacttggg   120
gatctgtccc ttgtggcacc agaagctaca acaggtncac ctggattcca gctctagctg   180
gactcggtaa ttgctaagtg ccagctctga agtctgtgat tccgtggaaa tccctttcaa   240
gcccgaattc tgttttttat gggcctcttg tccaaacagt ttgacttgtg aactctgttt   300
ctgtcaagtt gacacttggg cttggcaccc attcatgagc cagatgaaag cggctaaatg   360
cccgaaaaaa taaggnttt tacctttttt ttgaaccatt ggtgagcatn taaaaaaatt    420
agggaaggta aaacccaacc nggncaaacc caactnaaca nttttttttt ccnaaacaag   480 gggggggctan ttttttcactt ggaaaaacaa acaatttaa ttgantcttg ananggtgga  540
naaccaaaat tttttgttgg gttgggttcc gnagnccgaa tnntgcaaat ttctt        595
```

<210> SEQ ID NO 87
<211> LENGTH: 304
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 87

| | |
|---|---|
| cgtggcccga tgcattcagg gagccctctg tgttggccgc atagcaggtg tagttgccgg | 60 |
| catcctggat gaagacgggc gcgatctgta gaccccccga ttcaagaagc atgaacctag | 120 |
| gaatccggac agagccactg gccagaatgt ggttttctaa agaacagtgg agaaaagagg | 180 |
| catgttacag tcgtaacgct tgaaggaaat gaagatagtg gttagagcca taagcaagta | 240 |
| atatggttcg gctccgtgtc cccacccaag tctcgtctng aattgcaatc cccacgtcgg | 300 |
| cgca | 304 |

<210> SEQ ID NO 88
<211> LENGTH: 296
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 88

| | |
|---|---|
| ggctttcgnt aggagttaat ggggcattgg ngggtgggat ggcagggctg ccagcatctg | 60 |
| acccaggagg ctgggaggag ctgctgtgt gaatacacgc tcggcctctc acagtggctg | 120 |
| ccgccgcatt agccccttgt gcttcaggga acagagcatc cgtgatggat gagactttaa | 180 |
| ttaaagtaat gagacattta taatcgcggt tatctccaaa attaggcctt ttagcaatta | 240 |
| ttcctgggga atattcctcc ggtagatagc tccctttta gaacaacgtc ggcgca | 296 |

<210> SEQ ID NO 89
<211> LENGTH: 220
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 89

| | |
|---|---|
| attggcccgn caggcgggaa acangctgnn nttctctnac cgttntccag cactgcccag | 60 |
| accaggaggc gcaggagag gaggggncag cggttccgng accgctcctc ccgctgtccc | 120 |
| tgctctccag cctntgcctc tgcaggagcc cgcgggantt gccccaggcc cctgtcccca | 180 |
| cctgtggctc ccgtcctggt cgctcccggg gccgcggcaa | 220 |

<210> SEQ ID NO 90
<211> LENGTH: 273
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

```
<400> SEQUENCE: 90
gnagggnggn ggtcgcggac gccggtgggc agttcttgtt cggtgatgtg ggttaaaaag      60
gactgcagcg aggagccggg gcggcgctcg gagtaatcac cggcggcatc aaaaagcgcc     120
atcatggcat cgaggtcgcg gtctgcttgg gagccggtgg cgccgccgcg caaggcagat     180
gcctgcaggc gcatatccag ctcggtagcg ctccatacct cccacaggat ttcttccaca     240
gaggcttggg cttgtatagc ctgccgcccc gca                                  273

<210> SEQ ID NO 91
<211> LENGTH: 361
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 91
acggcttctn tnctaagtga cacggtgtgt gaaattcggt tggggaggta gttctgtaaa      60
ctgcgtctcc ccgccagcta aggaagttga gtgaagggag cgttgccgtc tgggaatcgt     120
agtcctcaca aaggcgtgag taggcggcaa ataaggattt gggtttagcc ttggggattc     180
actcctgtca aagctgttag agaagctccc anaactcnta aagtaacaga aactacttgc     240
ggcaacattt gtaacttcca cctggctcat tatcttccac tgttaccttg tgttctagat     300
aagttataat ttattctaca tatcgttcag aagtcttgtg cctgttccat attgtnagca     360
t                                                                     361

<210> SEQ ID NO 92
<211> LENGTH: 462
<212> TYPE: DNA
<213> ORGANISM: Homo sapiens

<400> SEQUENCE: 92
gctgcccaca ctggatggga aggaccggcg cctgcagcat ctgccctcca agccttcgta      60
gctccctcct tcctgcagga taaactctaa actccttagc acaacgtggg agccttctca     120
gagactgggt ccaacccatc tccagccgca gcctcccctc ctggccccac tgccacaccc     180
ccgggcctcc ggccacactg agcctctccc ggtttcccag gatacaacac tcgcccattc     240
atagtgtggt gccttttgca cgtgctgttc ctctgcttgg ggatgctgtt ggtctttctc     300
agccaggtga agaggacgct gaatgtcacc tgcttgagta tcaggaccgg ggactgggcg     360
ctggacctag actcttggcc ctggagagaa gccctgcatg gggccgcagc ctgccccgt     420 ccctgctcac agaaaagctc agccttgcag ccgcgtggga ga                       462

<210> SEQ ID NO 93
<211> LENGTH: 591
<212> TYPE: DNA
<213> ORGANISM: Homo sapiens

<400> SEQUENCE: 93
caaagtcacc tccacggtgc ggctcagcag ctcggcacac ttggtcatgg tgtcggggaa      60
ggcgccctcc agctgtaggt gggtagtggc agaacaggag ggtgagggga gagtccgaac     120
tgtccccact tggccgttcc ctccccactg gggggccctg agccagtggc ctcctctctc     180
ggggcctccc cggaaggagc caaggtctgt ctgcgaggca ccgtccccg gccacggcca      240 tcagccccca gaggtggatc aggcatcac ccccactcca cagctgaggc caggggggtca     300
```

-continued

```
gggaggcaac cagggcagac ctggaacctg gctctgagac aggacggccg agggcccctc    360
cactctccct ccctcggggt gggcactgac ctggacgcca agatgtcct cacactggtg     420 gcgtttgagt agggcccact cggacatctg gccctgcagc aggttggtgc agacggccat    480
ctctccacat gtcacatccg ccccgaagcg cttgcagatc cgtcggaagg gcaggttccc    540
acactgcggg gggagcagga cagacacaca tgctcttgca cgcgcacctc a             591
```

<210> SEQ ID NO 94
<211> LENGTH: 279
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 94

```
ttntgagttt tggcctgccc acagtctagc cctggacaga gaatccgagg ctcagccatg    60
ctgcagcacc caggacactg catcccagca cctgcccgaa aatcagccca gggacccaaa    120
ggaaagcagg ctccaagctc cccggaagcc aaggaaaata ggaaaacata tcctgccccg    180 gggacaccttt ctggaactat gaccacatgc acttgacctt ccggaacaat caccgcatgc   240
acctgacctc ccggaactgt caccaccgcg cgcacctca                           279
```

<210> SEQ ID NO 95
<211> LENGTH: 351
<212> TYPE: DNA
<213> ORGANISM: Homo sapiens

<400> SEQUENCE: 95

```
cctttattat tgttaaacgt cacccagaaa acccttaact cttagacagc ggctctcatt    60
aagcaaaagg ggaggcacat gaagctccag gcagggccgg gagggaaccg tgaagccaaa    120
ggctctggga gcccccaggc acctgcgttt gcatttcat cctggaggag accaggcctc     180
tggggctgct ccccggggtg cagagaggag gggtctttct tggtgtgtaa catactcatt    240
gattcagtca cctgaccttt gactccatgt attttgttga gtctggatgt gtggtgtgct    300
ctgcccagca gctgggatcc acatgagcac agacatggtc ccccgcggc a              351
```

<210> SEQ ID NO 96
<211> LENGTH: 171
<212> TYPE: DNA
<213> ORGANISM: Homo sapiens

<400> SEQUENCE: 96

```
ttgagtgtcg cgtgaatacc taggggacac tcagggaat gatggctccc ccgagaggta     60
aagggtggaa agaaggggcc tcagcaggtt aggtcttgct gggtccttct gtagggcgtc    120
tgggagatag atccgtgggg ctcctagggt cgcccctacc cggcgcgggc a              171
```

<210> SEQ ID NO 97
<211> LENGTH: 743
<212> TYPE: DNA
<213> ORGANISM: Homo sapiens
<220> FEATURE:
<221> NAME/KEY: misc_feature
<222> LOCATION: ()..()
<223> OTHER INFORMATION: "n" refers to an undetermined base

<400> SEQUENCE: 97

```
cctccctggc ccttgttccc aaggagcttc ccttgtccca gcctcttcgc cagtgacttc        60
tcactggacc attcctttac aaggagcctg ttttttgtgt ttttttttta cacctttttt       120
cttctatttc acagaaggaa caccggacgt ccctntgtga tggcagcagc catgctgcct       180
ntgtttccgc tcaggggttc tntgccacct ccaattccac ccagtctntt ggcctcggct       240
gggcttcggc tcccgcctnt gngccaaaaa ttgcaatgcc cgcggtcagg gncttttgcg       300
gagtctcacc gcctgcggag gcttgattcc ctcctcacag gcagcagcgt ttgatggccg       360
gtgacncccc cctttccaag cacatntntc atggcccctg aatgccactt acagggcgtc       420
cctccctgtg ctaagtgctg cctggancct tgggtgtggc agcagcaaan acctctaccc       480
ttgnggatgt tcgtttcggg gnggaaagac anatancaaa gttggtcgta aactgtaaag       540
tgtgctggga ggaaactgag gcagggaggg cctggtgcca ctggggagcn ctgccccgac       600
cccatgtgct tcccaggctc ccttggagcc acgtggatgg cgacttcctg accttggagg       660
ccgnggncct cantcctcat gctcgatggc gtcanccccc tcttggggaa atccaancat       720
tcctgacctg aaaatgcacc cnc                                               743
```

<210> SEQ ID NO 98
<211> LENGTH: 589
<212> TYPE: DNA
<213> ORGANISM: Homo sapiens

<400> SEQUENCE: 98

```
ttgccgcgct gataaaggaa gcgtctagaa ggtctcccca gccttcatca tctgagactt        60
ggctttcagc cccaaagcac taggccctgc tgttaacctt ccaccattaa cctttggtgc       120
tcttcaatta gcagcagcca ggggtccttg gcaggtatga gaatttggaa ggacagcccc       180
agggcatggc ccccggctgc agcaaaagtt ctaagtgttc ttctgttgga aggaagccca       240
ggagatattg atcagctgca ggtggggggag gccccagatc ccaccctttgc ctgcctccag       300
gagaaggttc tccatgggcc aaaatggagg cagagtccca ctttgcctgg gcagctccct       360
gagcatggct cccctgtggac ggagctgagt gacgtcatga ctctaggcct caacaaaaga       420
gctttggaaa atcccgatga ttcgaattgt attaaatcaa caaacatcgg gttgcacagt       480
tactagaaaa cggagatctg cgtcatcact tactagacac gtgaccttga acggcggctt       540
ccccgtgtga aacagcaaag ttctgtaacc cccatgaacg cgcctctca                   589
```

<210> SEQ ID NO 99
<211> LENGTH: 538
<212> TYPE: DNA
<213> ORGANISM: Homo sapiens

<400> SEQUENCE: 99

```
tgccgcgtct gaccctactc tcacaaagac tttccaacta gcataattga gttaaatggt        60
ccccccaact cccttaattc aagctaaact tgcagtttaa caactatagg agtgatatct       120
acacattaat gccacacttt aacatgccta acactacaca tgaacacgct tccgggtgct       180
gttacatccc gctctctccc aagcacgaga cacaggcagg atgctgacgt cctgcttctc       240
tgctgcgggc gggaagtcaa gactccggat ttgctgcagg agttgccgtg gggatcctga       300
cttcacgcag gagatggtcg gcctctggaa gtgcctggcc cgtttatcct tgaaatctac       360
ctgtgcaggt ggtccttgcc tcagcccctc aggacaacac aggtctttcc taagttacag       420
```

```
ggagaccatc agattgtcgt gtccgagccc cctgaagtgg aacccacagt ctccattcag    480
tctgccctca gtttccctcc cctctgcagg gccattgctg ctgtggacgc gcctctca     538

<210> SEQ ID NO 100
<211> LENGTH: 486
<212> TYPE: DNA
<213> ORGANISM: Homo sapiens

<400> SEQUENCE: 100
agaggtagaa aaaggagtta gaagcaaaga ggaaaaaata aataaacagg caacaaaaac     60
ccaacccagc cagcctgagc catttgcatt agtgttcatt taggaaatta gcagacggga    120
aacgctgggg agtggagtgg gccccggcct tggggactgc agagcccgct cagccctggg    180
tggctgggcc cacatgggct gtgccccagg agcacaggag gacccagagg gtggccgaga    240
gagcctcgcc gggctccggt atgggtcctg gcccctcaca ggtgcgagcc tggcccagtg    300
actgtggacg ctgtgggaga gcaggcctcc gatacgcagg gctgggactg ctgacctgga    360
aggtggtgcc gggcgtgtct ggtgaaggcg ccgttggcag ctagagagag acggcggatg    420
gggtgacgcc attacccacg gtcccagttt tgaggcttga cggtgacgga aaaggacgtc    480
ggcgca                                                              486

<210> SEQ ID NO 101
<211> LENGTH: 450
<212> TYPE: DNA
<213> ORGANISM: Homo sapiens

<400> SEQUENCE: 101
aattgaacca gggtgcacgg ccagcgccag acacagtgag cttcatggca actccagttt     60
accggtgaga accatggggc cactcagaga ggcaaagagc ctcacccgag tgagtcctct    120
ggcttctccc cacctgggcc gggcccagg ccgcgctgtg gttccctttc cagccgtcat    180
ccctgggtga tgggaggtgg gcattctgtt caaccttgtg ggtcagggag ccagggccag    240
tgtgcagatg agaagaggct gcggttactg gcgatgcgag ggactgtccc cttcgtgggc    300
actttctctt ttgaggccag tgaaatgtgt tccctggggt tgtattcctg agaaggcctc    360
atttaaaggg agccgccaaa ccaagtgggc ttagcaaaag cagtttgtca cctggcagca    420
cgtgtgagcc tcgcccggac gcgcctctca                                    450

<210> SEQ ID NO 102
<211> LENGTH: 292
<212> TYPE: DNA
<213> ORGANISM: Homo sapiens

<400> SEQUENCE: 102
agcgcggcct ggcagattgc ccattaatga aactcagtgg gcagaggctg ctgagggaca     60
cggattccca ctccccgggg gagggggtgg aaatggcttc ctccctctgc ttccctacca    120
ccagtaatgg ggagctcacc atgcttagaa gactcttcct tgcatggagt tcgggcctcc    180
tccctgcacc taccacccta gtggcccaa gtcttaaggc tgaaggttaa tcctgtgtcc    240
ttcagaagca aaggctgcaa ccgataccaa acagaggtgg ccagcgcggg ca            292

<210> SEQ ID NO 103
<211> LENGTH: 395
<212> TYPE: DNA
<213> ORGANISM: Homo sapiens
```

```
-continued

<220> FEATURE:
<221> NAME/KEY: misc_feature
<222> LOCATION: ()..()
<223> OTHER INFORMATION: "n" refers to an undetermined base

<400> SEQUENCE: 103
agagcttatc ccgcgagcac aagggagccg gggcctgggc cgccgtggga aggggctcct       60
gccttccggg gacgcggtca gggaagtcca gccggggtgc tctctgcact gcgggtgccg      120
ggctcggcag aggccaaccc ggcaaaacga gcaggatctc ccggcccac cctagtgggc       180 tccgcctgcc ccaacaacca tcctgccatc ctccctgcga gacaggtgac tttcctctct      240
gatgcggtgc atctgtcatc tgtctaacgg gcccattccc cagtgaaaca cccccaacca     300
aagacacgaa ggggaaggcg caagcttcta ccaagctcan tttgcccatc tggtgcccac     360
ctgcctngta tttggtgact tggaggatag gaagg                                395
```